(12) United States Patent
McCaffrey et al.

(10) Patent No.: US 11,045,603 B2
(45) Date of Patent: Jun. 29, 2021

(54) NEEDLE INSERTION MECHANISMS FOR DRUG CONTAINERS

(71) Applicant: Insulet Corporation, Acton, MA (US)

(72) Inventors: Maureen McCaffrey, Boston, MA (US); Ian McLaughlin, Boxboro, MA (US)

(73) Assignee: INSULET CORPORATION, Acton, MA (US)

( * ) Notice: Subject to any disclaimer, the term of this patent is extended or adjusted under 35 U.S.C. 154(b) by 141 days.

(21) Appl. No.: 15/901,082

(22) Filed: Feb. 21, 2018

(65) Prior Publication Data
US 2018/0236173 A1     Aug. 23, 2018

Related U.S. Application Data

(60) Provisional application No. 62/462,178, filed on Feb. 22, 2017, provisional application No. 62/540,698, filed on Aug. 3, 2017.

(51) Int. Cl.
*A61M 5/24* (2006.01)
*A61M 5/20* (2006.01)
(Continued)

(52) U.S. Cl.
CPC ...... *A61M 5/2466* (2013.01); *A61M 5/14244* (2013.01); *A61M 5/14248* (2013.01);
(Continued)

(58) Field of Classification Search
CPC .... A61M 5/2466; A61M 5/285; A61M 5/288; A61M 5/14244; A61M 5/14248;
(Continued)

(56) References Cited

U.S. PATENT DOCUMENTS 303,013 A    8/1884   Horton
306,691 A   10/1884   Johnson
(Continued)

FOREIGN PATENT DOCUMENTS

DE    19723648 C1    8/1998
DE    19920896 A1   11/2000
(Continued)

OTHER PUBLICATIONS

US 5,954,699 A, 09/1999, Jost et al. (withdrawn)
(Continued)

*Primary Examiner* — Kevin C Sirmons
*Assistant Examiner* — Antarius S Daniel
(74) *Attorney, Agent, or Firm* — Kacvinsky Daisak Bluni PLLC

(57) ABSTRACT

Systems for piercing a septum of a drug delivery device is disclosed. The drug delivery device may include a needle conduit having an end and a drug container having a septum. The septum piercing mechanism may include a needle support operatively coupled to the needle conduit. The septum piercing mechanism may be movable from a first, unactivated configuration to a second, activated configuration. In the unactivated configuration, the septum seals an interior of the drug container from the end of the needle conduit. In the activated configuration, the end of the needle conduit pierces through the septum placing the needle conduit in fluid communication with the drug container. In one embodiment, activation may cause the needle support to move towards the drug container. In one embodiment, the needle support may be moved by a biasing member. Alternatively, in another embodiment, the needle support may be moved by a cam mechanism.

9 Claims, 16 Drawing Sheets

(51) Int. Cl.
*A61M 5/142* (2006.01)
*A61M 5/28* (2006.01)
*A61M 5/162* (2006.01)
*A61M 5/32* (2006.01)
*A61M 5/145* (2006.01)
*A61M 5/315* (2006.01)
*A61M 5/158* (2006.01)

(52) U.S. Cl.
CPC .......... *A61M 5/162* (2013.01); *A61M 5/2033* (2013.01); *A61M 5/288* (2013.01); *A61M 5/14566* (2013.01); *A61M 5/3202* (2013.01); *A61M 2005/14252* (2013.01); *A61M 2005/1581* (2013.01); *A61M 2005/1585* (2013.01); *A61M 2005/208* (2013.01); *A61M 2005/2474* (2013.01); *A61M 2005/31518* (2013.01); *A61M 2205/3386* (2013.01); *A61M 2205/58* (2013.01); *A61M 2205/82* (2013.01)

(58) Field of Classification Search
CPC .. A61M 5/162; A61M 5/2033; A61M 5/3287; A61M 2005/2474; A61M 2005/14252; A61M 2005/206
See application file for complete search history.

(56) References Cited

U.S. PATENT DOCUMENTS

| | | |
|---|---|---|
| 315,727 A | 4/1885 | Church |
| 405,524 A | 6/1889 | Benton |
| 410,817 A | 9/1889 | Weeks, Jr. |
| 2,667,986 A | 2/1954 | Perelson |
| 3,631,847 A | 1/1972 | Hobbs |
| 3,792,703 A | 2/1974 | Moorehead |
| 3,812,843 A | 5/1974 | Wootten |
| 3,841,328 A | 10/1974 | Jensen |
| 3,885,662 A | 5/1975 | Schaefer |
| 4,067,000 A | 1/1978 | Carlson |
| 4,151,845 A | 5/1979 | Clemens |
| 4,152,098 A | 5/1979 | Moody et al. |
| 4,193,397 A | 3/1980 | Tucker et al. |
| 4,211,998 A | 7/1980 | Junginger et al. |
| 4,231,019 A | 10/1980 | Junginger et al. |
| 4,261,388 A | 4/1981 | Shelton |
| 4,268,150 A | 5/1981 | Chen |
| 4,276,170 A | 6/1981 | Vaillancourt |
| 4,342,311 A | 8/1982 | Whitney et al. |
| 4,346,385 A | 8/1982 | Schiavone et al. |
| 4,364,385 A | 12/1982 | Lossef |
| 4,424,720 A | 1/1984 | Bucchianeri |
| 4,435,173 A | 3/1984 | Siposs et al. |
| 4,469,481 A | 9/1984 | Kobayashi |
| 4,475,901 A | 10/1984 | Kraegen et al. |
| 4,498,843 A | 2/1985 | Schneider et al. |
| 4,507,115 A | 3/1985 | Kambara et al. |
| 4,514,732 A | 4/1985 | Hayes, Jr. |
| 4,529,401 A | 7/1985 | Leslie et al. |
| 4,551,134 A | 11/1985 | Slavik et al. |
| 4,559,033 A | 12/1985 | Stephen et al. |
| 4,559,037 A | 12/1985 | Franetzki et al. |
| 4,560,979 A | 12/1985 | Rosskopf |
| 4,562,751 A | 1/1986 | Nason et al. |
| 4,585,439 A | 4/1986 | Michel |
| 4,601,707 A | 7/1986 | Albisser et al. |
| 4,624,661 A | 11/1986 | Arimond |
| 4,634,427 A | 1/1987 | Hannula et al. |
| 4,678,408 A | 7/1987 | Nason et al. |
| 4,684,368 A | 8/1987 | Kenyon |
| 4,685,903 A | 8/1987 | Cable et al. |
| 4,734,092 A | 3/1988 | Millerd |
| 4,743,243 A | 5/1988 | Vaillancourt |
| 4,755,173 A | 7/1988 | Konopka et al. |
| 4,781,688 A | 11/1988 | Thoma et al. |
| 4,781,693 A | 11/1988 | Martinez et al. |
| 4,801,957 A | 1/1989 | Vandemoere |
| 4,808,161 A | 2/1989 | Kamen |
| 4,836,752 A | 6/1989 | Burkett |
| 4,855,746 A | 8/1989 | Stacy |
| 4,858,619 A | 8/1989 | Toth |
| 4,871,351 A | 10/1989 | Feingold |
| 4,882,600 A | 11/1989 | Van de Moere |
| 4,886,499 A | 12/1989 | Cirelli et al. |
| 4,898,578 A | 2/1990 | Rubalcaba, Jr. |
| 4,898,579 A | 2/1990 | Groshong et al. |
| 4,944,659 A | 7/1990 | Labbe et al. |
| 4,969,874 A | 11/1990 | Michel et al. |
| 4,973,998 A | 11/1990 | Gates |
| 4,985,016 A | 1/1991 | Theeuwes et al. |
| 4,994,047 A | 2/1991 | Walker et al. |
| 5,007,458 A | 4/1991 | Marcus et al. |
| 5,045,871 A | 9/1991 | Reinholdson |
| 5,062,841 A | 11/1991 | Siegel |
| 5,109,850 A | 5/1992 | Blanco et al. |
| 5,125,415 A | 6/1992 | Bell |
| 5,176,662 A | 1/1993 | Bartholomew et al. |
| 5,178,609 A | 1/1993 | Ishikawa |
| 5,189,609 A | 2/1993 | Tivig et al. |
| 5,205,819 A | 4/1993 | Ross et al. |
| 5,213,483 A | 5/1993 | Flaherty et al. |
| 5,232,439 A | 8/1993 | Campbell et al. |
| 5,239,326 A | 8/1993 | Takai |
| 5,244,463 A | 9/1993 | Cordner, Jr. et al. |
| 5,245,447 A | 9/1993 | Stemmle |
| 5,254,096 A | 10/1993 | Rondelet et al. |
| 5,257,980 A | 11/1993 | Van Antwerp et al. |
| 5,261,884 A | 11/1993 | Stern et al. |
| 5,281,202 A | 1/1994 | Weber et al. |
| 5,308,335 A | 5/1994 | Ross et al. |
| 5,312,337 A | 5/1994 | Flaherty et al. |
| 5,318,540 A | 6/1994 | Athayde et al. |
| 5,342,313 A | 8/1994 | Campbell et al. |
| 5,346,476 A | 9/1994 | Elson |
| 5,364,342 A | 11/1994 | Beuchat et al. |
| 5,411,480 A | 5/1995 | Kriesel |
| 5,433,710 A | 7/1995 | VanAntwerp et al. |
| 5,452,033 A | 9/1995 | Balling et al. |
| 5,492,534 A | 2/1996 | Athayde et al. |
| 5,503,628 A | 4/1996 | Fetters et al. |
| 5,505,709 A | 4/1996 | Funderburk et al. |
| 5,507,288 A | 4/1996 | Bocker et al. |
| 5,514,096 A | 5/1996 | Hiejima |
| 5,533,389 A | 7/1996 | Kamen et al. |
| 5,545,152 A | 8/1996 | Funderburk et al. |
| 5,573,342 A | 11/1996 | Patalano |
| 5,575,770 A | 11/1996 | Melsky et al. |
| 5,576,781 A | 11/1996 | Deleeuw |
| 5,582,593 A | 12/1996 | Hultman |
| 5,584,813 A | 12/1996 | Livingston et al. |
| 5,613,956 A | 3/1997 | Patterson et al. |
| 5,630,710 A | 5/1997 | Tune et al. |
| 5,637,095 A | 6/1997 | Nason et al. |
| 5,643,213 A | 7/1997 | McPhee |
| 5,647,853 A | 7/1997 | Feldmann et al. |
| 5,665,065 A | 9/1997 | Colman et al. |
| 5,665,070 A | 9/1997 | McPhee |
| 5,678,539 A | 10/1997 | Schubert et al. |
| 5,685,859 A | 11/1997 | Kornerup |
| 5,693,018 A | 12/1997 | Kriesel et al. |
| 5,695,490 A | 12/1997 | Flaherty et al. |
| 5,702,363 A | 12/1997 | Flaherty |
| 5,704,520 A | 1/1998 | Gross |
| 5,716,343 A | 2/1998 | Kriesel et al. |
| 5,726,404 A | 3/1998 | Brody |
| 5,726,751 A | 3/1998 | Altendorf et al. |
| 5,741,228 A | 4/1998 | Lambrecht et al. |
| 5,747,350 A | 5/1998 | Sattler |
| 5,748,827 A | 5/1998 | Holl et al. |
| 5,755,682 A | 5/1998 | Knudson et al. |
| 5,764,159 A | 6/1998 | Neftel |
| 5,776,103 A | 7/1998 | Kriesel et al. |
| 5,779,676 A | 7/1998 | Kriesel et al. |
| 5,785,681 A | 7/1998 | Indravudh |
| 5,785,688 A | 7/1998 | Joshi et al. |

(56) References Cited

U.S. PATENT DOCUMENTS

| | | | |
|---|---|---|---|
| 5,797,881 A | 8/1998 | Gadot | |
| 5,800,397 A | 9/1998 | Wilson et al. | |
| 5,800,405 A | 9/1998 | McPhee | |
| 5,800,420 A | 9/1998 | Gross et al. | |
| 5,810,015 A | 9/1998 | Flaherty | |
| 5,814,020 A | 9/1998 | Gross | |
| 5,840,063 A | 11/1998 | Flaherty | |
| 5,845,218 A | 12/1998 | Altschul | |
| 5,848,990 A * | 12/1998 | Cirelli | A61M 5/158 604/136 |
| 5,848,991 A | 12/1998 | Gross et al. | |
| 5,851,197 A | 12/1998 | Marano et al. | |
| 5,858,005 A | 1/1999 | Kriesel | |
| 5,858,239 A | 1/1999 | Kenley et al. | |
| 5,865,806 A | 2/1999 | Howell | |
| 5,871,470 A | 2/1999 | McWha | |
| 5,875,393 A | 2/1999 | Altschul et al. | |
| 5,878,539 A | 3/1999 | Grubb | |
| 5,885,808 A | 3/1999 | Spooner et al. | |
| 5,886,647 A | 3/1999 | Badger et al. | |
| 5,891,097 A | 4/1999 | Saito et al. | |
| 5,897,530 A | 4/1999 | Jackson | |
| 5,906,597 A | 5/1999 | McPhee | |
| 5,911,716 A | 6/1999 | Rake et al. | |
| 5,919,167 A | 7/1999 | Mulhauser et al. | |
| 5,921,419 A | 7/1999 | Niedospial, Jr. et al. | |
| 5,931,814 A | 8/1999 | Alex et al. | |
| 5,935,099 A | 8/1999 | Peterson et al. | |
| 5,954,058 A | 9/1999 | Flaherty | |
| 5,954,694 A | 9/1999 | Sunseri | |
| 5,957,890 A | 9/1999 | Mann et al. | |
| 5,957,895 A | 9/1999 | Sage et al. | |
| 5,961,492 A | 10/1999 | Kriesel et al. | |
| 5,965,848 A | 10/1999 | Altschul et al. | |
| 5,983,094 A | 11/1999 | Altschul et al. | |
| 5,993,423 A | 11/1999 | Choi | |
| 5,997,501 A | 12/1999 | Gross et al. | |
| 6,019,747 A | 2/2000 | McPhee | |
| 6,024,539 A | 2/2000 | Blomquist | |
| 6,050,978 A | 4/2000 | Orr et al. | |
| 6,071,292 A | 6/2000 | Makower et al. | |
| 6,090,092 A | 7/2000 | Fowles et al. | |
| 6,126,637 A | 10/2000 | Kriesel et al. | |
| 6,144,847 A | 11/2000 | Altschul et al. | |
| 6,152,898 A | 11/2000 | Olsen | |
| 6,174,300 B1 | 1/2001 | Kriesel et al. | |
| 6,190,359 B1 | 2/2001 | Heruth | |
| 6,200,338 B1 | 3/2001 | Solomon et al. | |
| 6,206,850 B1 | 3/2001 | ONeil | |
| 6,244,776 B1 | 6/2001 | Wiley | |
| 6,244,778 B1 | 6/2001 | Chesbrough | |
| 6,309,370 B1 | 10/2001 | Haim et al. | |
| 6,363,609 B1 | 4/2002 | Pickren | |
| 6,375,639 B1 | 4/2002 | Duplessie et al. | |
| 6,475,196 B1 | 11/2002 | Vachon | |
| 6,520,936 B1 | 2/2003 | Mann | |
| 6,527,744 B1 | 3/2003 | Kriesel et al. | |
| 6,569,125 B2 | 5/2003 | Jepson et al. | |
| 6,572,542 B1 | 6/2003 | Houben et al. | |
| 6,572,585 B2 | 6/2003 | Choi | |
| 6,666,852 B2 | 12/2003 | Niedospial, Jr. | |
| 6,699,221 B2 | 3/2004 | Vaillancourt | |
| 6,740,059 B2 | 5/2004 | Flaherty | |
| 6,883,778 B1 | 4/2005 | Newton et al. | |
| 7,008,404 B2 | 3/2006 | Nakajima | |
| 7,018,360 B2 | 3/2006 | Flaherty et al. | |
| 7,025,744 B2 | 4/2006 | Utterberg et al. | |
| 7,060,059 B2 | 6/2006 | Keith et al. | |
| 7,128,727 B2 | 10/2006 | Flaherty et al. | |
| 7,144,384 B2 | 12/2006 | Gorman et al. | |
| 7,160,272 B1 | 1/2007 | Eyal et al. | |
| 7,267,665 B2 | 9/2007 | Steil et al. | |
| 7,291,133 B1 | 11/2007 | Kindler et al. | |
| 7,303,549 B2 | 12/2007 | Flaherty et al. | |
| 7,918,825 B2 | 4/2011 | O'Connor et al. | |
| 9,402,950 B2 | 8/2016 | Dilanni et al. | |
| 2001/0053895 A1 | 12/2001 | Vaillancourt | |
| 2002/0010423 A1 | 1/2002 | Gross et al. | |
| 2002/0032374 A1 | 3/2002 | Holker et al. | |
| 2002/0066715 A1 | 6/2002 | Niedospial | |
| 2002/0123740 A1 | 9/2002 | Flaherty et al. | |
| 2003/0163097 A1 | 8/2003 | Fleury et al. | |
| 2004/0010207 A1 | 1/2004 | Flaherty et al. | |
| 2004/0064088 A1 | 4/2004 | Gorman et al. | |
| 2004/0088224 A1 | 5/2004 | Mukai | |
| 2004/0092865 A1 | 5/2004 | Flaherty et al. | |
| 2004/0116847 A1 | 6/2004 | Wall | |
| 2004/0158208 A1 | 8/2004 | Hiejima | |
| 2004/0203357 A1 | 10/2004 | Nassimi | |
| 2005/0020980 A1 | 1/2005 | Inoue et al. | |
| 2005/0187524 A1 | 8/2005 | Willis et al. | |
| 2005/0203461 A1 * | 9/2005 | Flaherty | A61M 5/14248 604/131 |
| 2005/0238507 A1 | 10/2005 | Dilanni et al. | |
| 2005/0258581 A1 | 11/2005 | Tanaka | |
| 2006/0134323 A1 | 6/2006 | O'Brien | |
| 2006/0155210 A1 | 7/2006 | Beckman et al. | |
| 2006/0178633 A1 | 8/2006 | Garibotto et al. | |
| 2006/0204535 A1 | 9/2006 | Johnson | |
| 2006/0253085 A1 | 11/2006 | Geismar et al. | |
| 2006/0282290 A1 | 12/2006 | Flaherty et al. | |
| 2007/0005018 A1 | 1/2007 | Tekbuchava | |
| 2007/0025811 A1 | 2/2007 | Wilhelm | |
| 2007/0112332 A1 | 5/2007 | Harding et al. | |
| 2007/0118405 A1 | 5/2007 | Campbell et al. | |
| 2007/0129690 A1 | 6/2007 | Rosenblatt et al. | |
| 2007/0173974 A1 | 7/2007 | Lin | |
| 2007/0197163 A1 | 8/2007 | Robertson | |
| 2007/0282269 A1 | 12/2007 | Carter et al. | |
| 2008/0004515 A1 | 1/2008 | Jennewine | |
| 2008/0006500 A1 | 1/2008 | Spahr | |
| 2008/0051738 A1 | 2/2008 | Griffin | |
| 2008/0065050 A1 | 3/2008 | Sparks et al. | |
| 2008/0078400 A1 | 4/2008 | Martens et al. | |
| 2008/0132880 A1 | 6/2008 | Buchman | |
| 2008/0249508 A1 | 10/2008 | Lopez et al. | |
| 2008/0287906 A1 | 11/2008 | Burkholz et al. | |
| 2009/0062767 A1 | 3/2009 | Van Antwerp et al. | |
| 2009/0069787 A1 | 3/2009 | Estes et al. | |
| 2009/0099521 A1 | 4/2009 | Gravesen et al. | |
| 2009/0124979 A1 | 5/2009 | Raymond et al. | |
| 2009/0198215 A1 | 8/2009 | Chong et al. | |
| 2009/0299300 A1 | 12/2009 | Truitt et al. | |
| 2010/0137784 A1 | 6/2010 | Cefai et al. | |
| 2010/0152658 A1 | 6/2010 | Hanson et al. | |
| 2011/0054390 A1 * | 3/2011 | Searle | A61M 5/1413 604/66 |
| 2011/0054399 A1 | 3/2011 | Chong et al. | |
| 2011/0144586 A1 | 6/2011 | Michaud et al. | |
| 2011/0166512 A1 * | 7/2011 | Both | A61M 5/14248 604/67 |
| 2011/0230833 A1 | 9/2011 | Landman et al. | |
| 2011/0251509 A1 | 10/2011 | Beyhan et al. | |
| 2011/0316562 A1 | 12/2011 | Cefai et al. | |
| 2012/0003093 A1 | 1/2012 | Lischer et al. | |
| 2012/0003935 A1 | 1/2012 | Lydon et al. | |
| 2012/0010594 A1 | 1/2012 | Holt et al. | |
| 2012/0078161 A1 | 3/2012 | Masterson et al. | |
| 2012/0238851 A1 | 9/2012 | Kamen et al. | |
| 2012/0277668 A1 | 11/2012 | Chawla | |
| 2013/0060233 A1 | 3/2013 | O'Connor et al. | |
| 2013/0178791 A1 | 7/2013 | Javitt | |
| 2013/0317753 A1 | 11/2013 | Kamen et al. | |
| 2014/0074033 A1 | 3/2014 | Sonderegger et al. | |
| 2014/0127048 A1 | 5/2014 | Diianni et al. | |
| 2014/0128839 A1 | 5/2014 | Diianni et al. | |
| 2014/0135880 A1 | 5/2014 | Bumgartner et al. | |
| 2014/0316379 A1 | 10/2014 | Sonderegger et al. | |
| 2016/0015891 A1 | 1/2016 | Papiorek | |
| 2016/0038689 A1 | 2/2016 | Lee et al. | |

(56) References Cited

U.S. PATENT DOCUMENTS

| | | |
|---|---|---|
| 2016/0302054 A1 | 10/2016 | Kimura et al. |
| 2017/0128664 A1 | 5/2017 | Diianni et al. |

FOREIGN PATENT DOCUMENTS

| | | |
|---|---|---|
| EP | 0341049 A2 | 11/1989 |
| EP | 0496305 A2 | 7/1992 |
| EP | 0763369 A1 | 3/1997 |
| EP | 0867196 A2 | 9/1998 |
| EP | 0937475 A2 | 8/1999 |
| EP | 2397181 A1 | 12/2011 |
| EP | 2830499 A1 | 2/2015 |
| GB | 875034 A | 8/1961 |
| GB | 2443261 A | 4/2008 |
| TW | 200740148 A | 10/2007 |
| TW | M452390 U | 5/2013 |
| WO | 8101658 A1 | 6/1981 |
| WO | 8606796 A1 | 11/1986 |
| WO | 9800193 A1 | 1/1998 |
| WO | 9801071 A1 | 1/1998 |
| WO | 9856293 A1 | 12/1998 |
| WO | 9910040 A1 | 3/1999 |
| WO | 9956803 A1 | 11/1999 |
| WO | 9962576 A1 | 12/1999 |
| WO | 0019887 A1 | 4/2000 |
| WO | 0029047 A1 | 5/2000 |
| WO | 0029049 A1 | 5/2000 |
| WO | 0030705 A1 | 6/2000 |
| WO | 0061215 A1 | 10/2000 |
| WO | 0074752 A1 | 12/2000 |
| WO | 0078210 A1 | 12/2000 |
| WO | 0152727 A1 | 7/2001 |
| WO | 0156633 A2 | 8/2001 |
| WO | 0176684 A1 | 10/2001 |
| WO | 200172354 A2 | 10/2001 |
| WO | 2002015954 A1 | 2/2002 |
| WO | 0220073 A2 | 3/2002 |
| WO | 0226282 A2 | 4/2002 |
| WO | 0240083 A2 | 5/2002 |
| WO | 2002068823 A1 | 9/2002 |
| WO | 03090509 A2 | 11/2003 |
| WO | 2006053007 A2 | 5/2006 |
| WO | 2016141082 A1 | 9/2006 |
| WO | 2007064835 A2 | 6/2007 |
| WO | 2008024810 A2 | 2/2008 |
| WO | 2008133702 A1 | 11/2008 |
| WO | 2009098648 A2 | 8/2009 |
| WO | 2011095483 A1 | 8/2011 |
| WO | 20120045667 A2 | 4/2012 |
| WO | 2012108959 A1 | 8/2012 |
| WO | 2012134588 A1 | 10/2012 |
| WO | 2013078200 A1 | 5/2013 |
| WO | 2013134486 A2 | 9/2013 |
| WO | 2013149186 A1 | 10/2013 |
| WO | 2013182321 A1 | 12/2013 |
| WO | 2014194183 A2 | 12/2014 |
| WO | 2015061493 A1 | 4/2015 |
| WO | 2015081337 A2 | 6/2015 |
| WO | 2017205816 A1 | 11/2017 |

OTHER PUBLICATIONS

International Search Report and Written Opinion for application No. PCT/US2017/015601, dated May 16, 2017, 12 pages.

International Search Report and Written Opinion for Application No. PCT/US2018/052464, dated Jan. 4, 2019, 13 pages.

International Search Report and Written Opinion of PCT/US2018/018901, dated: Aug. 6, 2018, 15 pages.

International Preliminary Report on Patentability for the International Patent Application No. PCT/US2018/018901, dated Sep. 6, 2019, 8 pages.

International Preliminary Report on Patentability dated Oct. 9, 2014, issued in PCT Patent Application No. PCT/US2013/034674, 15 pages.

EPO Search Report dated Nov. 11, 2015, received in corresponding Application No. 13768938.6, 7 pgs.

European Patent Office, "Notification of Transmittal of the ISR and the Written Opinion of the International Searching Authority, or the Declaration," in PCT Application No. PCT/GB2015/050248, dated Jun. 23, 2015, 12 pages.

U.K. Intellectual Property Office, GB Application No. GB 1401591.1, ""Search Report underSection 17(5)"" dated Jul. 9, 2015, 3 pages.

International Preliminary Report on Patentability dated Apr. 9, 2020, issued in PCT Patent Application No. PCT/US2018/052464, 7 pages.

International Search Report for the International Patent Application No. PCT/US03/16640, dated Oct. 3, 2003, 1 page.

User's Guide for Model 508 Insulin Pump, Mini Med, Aug. 2000, 145 pages.

Web-Site Brochure dated Jan. 4, 2000. SOOIL-Homepage. "Portable Insulin Pump". www.sooil.com/product2.htm.

Web-Site Brochure dated Jan. 4, 2000. SOOIL-Homepage. ""Portable Insulin Pump"".www.sooil.com/product3.htm.

Web-Site Brochure dated Jan. 4, 2000. SOOIL-Homepage. "Portable Insulin Pump". www.sooil.com/product4.htm.

Web-Site Brochure dated Dec. 20, 1999. "The Animas R-1000 Insulin Pump". www .animascorp.com/pump f _ s.html.

Web-Site Brochure dated Dec. 20, 1999. ""The Animas R-1000 Insulin Pump"" www.animascorp.com/pump_f_f.html.

Web-Site Brochure dated Jan. 4, 2000. SOOIL-Homepage. ""Ponable Insulin Pump"".www.sooil.com/intro2.htm.

Web-Site Brochure dated Jan. 4, 2000. MiniMed 508. "Doing its job. Naturally." www.minimed.com/tiles/mm 113.htm.

Web-Site Brochure dated Dec. 20, 1999. Applied Medical Technology. ""508 Pump Information"". www.applied-medical.co.uk/508.htm.

Web-Site Brochure dated Jan. 4, 2000. ""The Glucose Sensor"". www.animascorp.corn/sensor f.html.

* cited by examiner

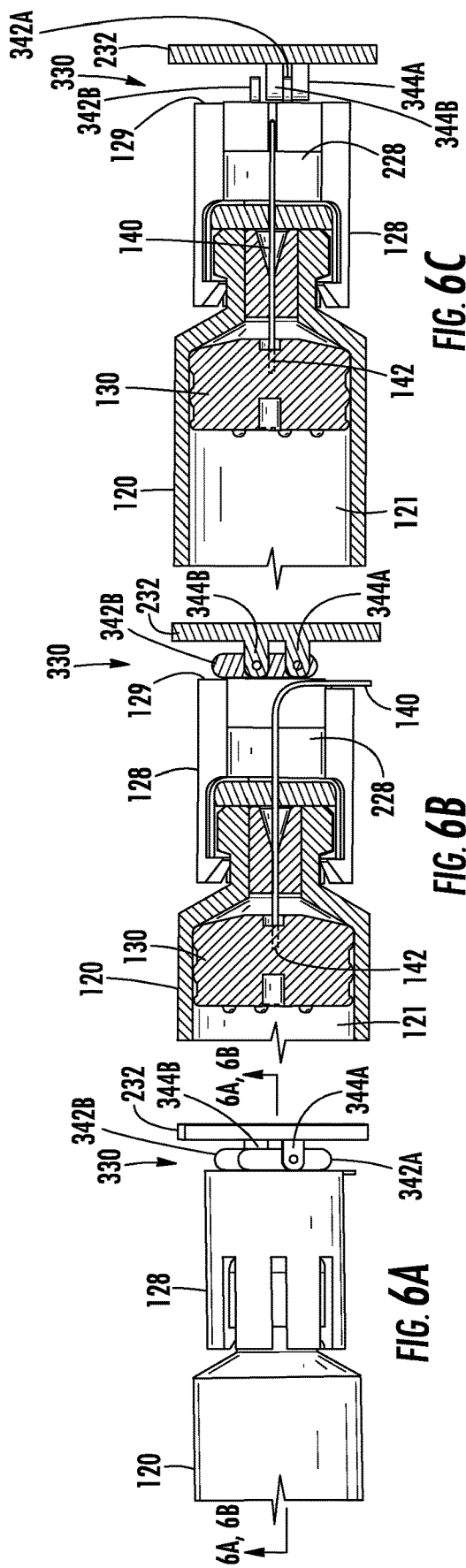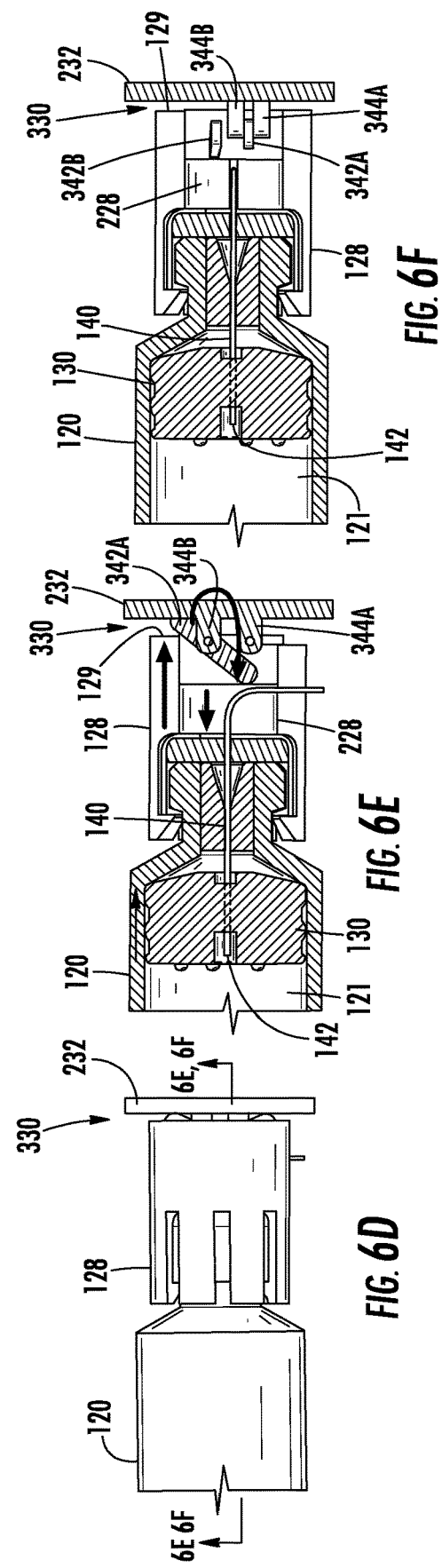

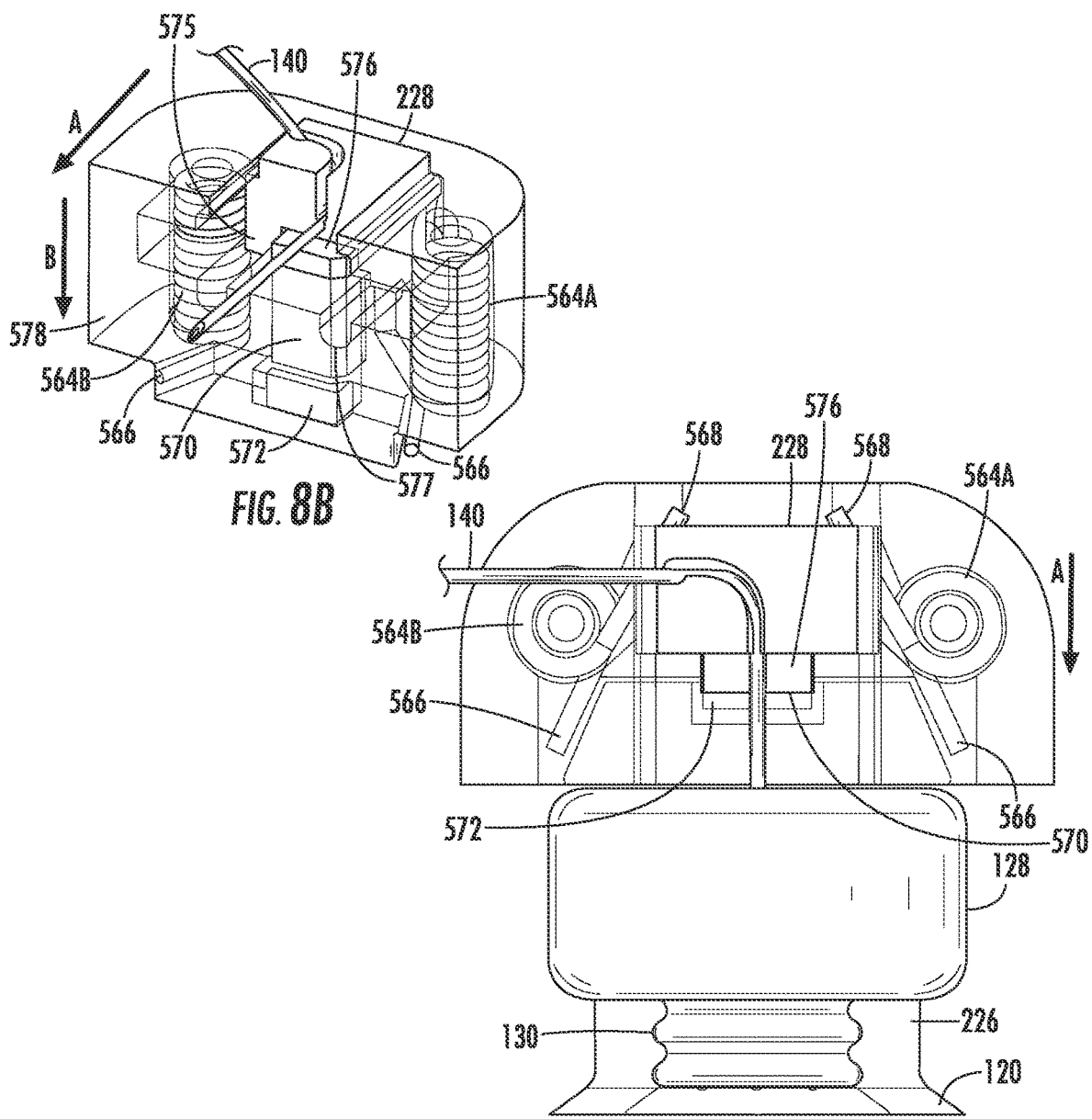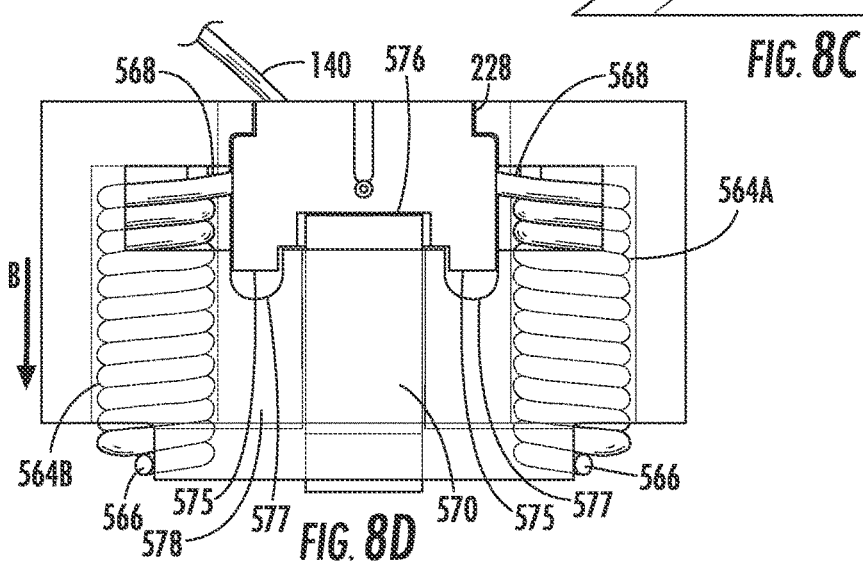

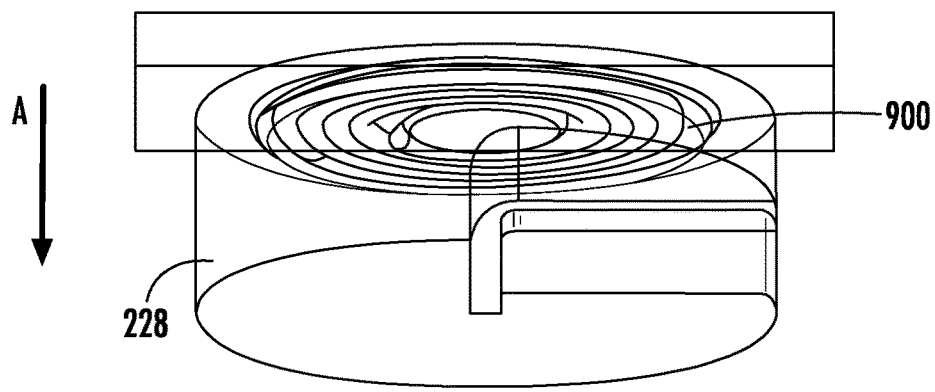
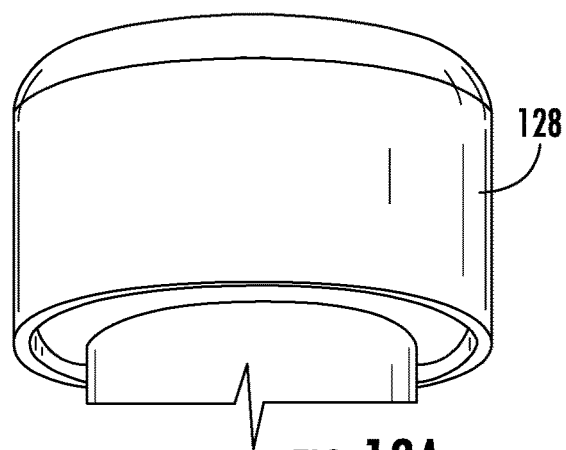
FIG. 13A
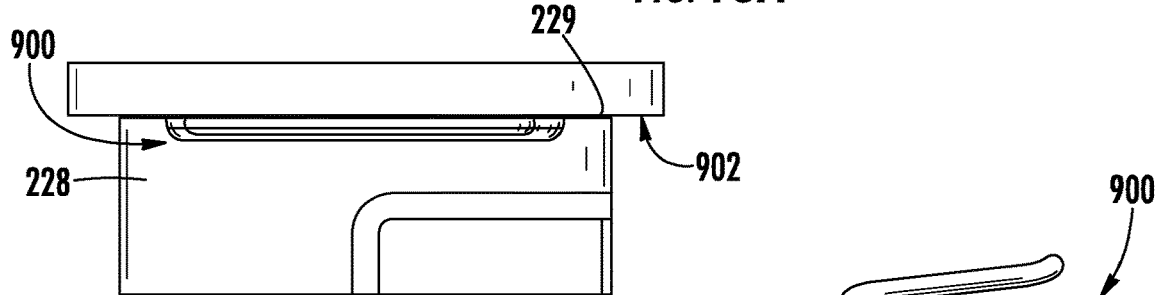
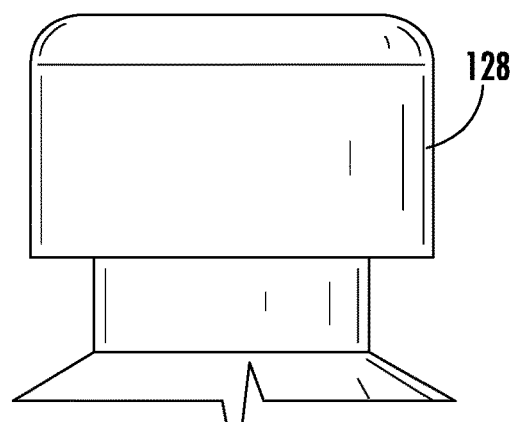
FIG. 13B
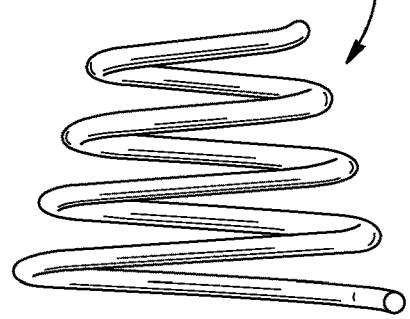
FIG. 13C

NEEDLE INSERTION MECHANISMS FOR DRUG CONTAINERS

CROSS-REFERENCE TO RELATED APPLICATIONS

This application claims the benefit of U.S. Provisional Application No. 62/462,178, filed Feb. 22, 2017, and U.S. Provisional Application No. 62/540,698, filed Aug. 3, 2017, each of which is incorporated herein by reference in its entirety.

TECHNICAL FIELD

The present disclosure generally relates to medication delivery devices, and more particularly to a septum piercing mechanism for piercing a septum located on a drug container to enable fluid communication between the liquid drug contained in the drug container and a needle injection mechanism for delivery to a patient.

BACKGROUND

Drug delivery devices including, but not limited to, wearable drug delivery devices, can be provided to a user with a liquid drug prefilled in a drug container located or positionable within the drug delivery device. For such devices, it may it may be beneficial to keep the fluid path (e.g., the needle and/or fluid conduit) separate from the liquid drug until the time of use. That is, it may be beneficial to maintain the fluid path out of fluid communication with the liquid drug contained in the drug container until the moment it is needed to be delivered to the patient. As will be appreciated, the liquid drug may reside in the drug container within the drug delivery device during its entire shelf life. If the fluid path were mated with the liquid drug while, for example, on the shelf, the septum (e.g., the seal located at one end of the drug container) could stress relax around the needle, which could affect the integrity of the seal. It could also affect drug stability.

Accordingly, there is a need for an improved device, system and method for joining the fluid path with the liquid drug within a drug delivery device when the drug delivery device is activated to provide the liquid drug to a user.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

Disclosed herein is a drug delivery device for administering a liquid drug stored in a drug container located within the drug delivery device to a patient. In one embodiment, the drug delivery device includes a drug container, a needle insertion mechanism, a needle conduit, and a septum piercing mechanism. The drug container may include a liquid drug and a septum at one end of the drug container for sealing the liquid drug within the drug container. The needle insertion mechanism is adapted and configured for insertion into the patient for administering the liquid drug. The needle conduit includes a first end operatively associated with the drug container and a second end coupled to the needle insertion mechanism. The septum piercing mechanism is adapted and configured for piercing the septum of the drug container. The septum piercing mechanism may include a needle support operatively coupled with the first end of the needle conduit and a biasing member operatively coupled to the needle support to bias the needle support towards the drug container.

In use, the septum piercing mechanism is movable between an unactivated configuration and an activated configuration. In the unactivated configuration, the first end of the needle conduit is separated from the liquid drug stored in the drug container via the septum. In the activated configuration, the first end of the needle conduit pierces through the septum so that the needle conduit is in fluid communication with the liquid drug stored in the drug container.

In one embodiment, in the unactivated configuration, the needle support is prevented from moving towards the drug container. In the activated configuration, the needle support is permitted to move towards the drug container such that the first end of the needle conduit pierces the septum, exposing the first end of the needle conduit to an interior portion of the drug container.

In one embodiment, the drug container is fixedly positioned within the drug delivery device such that the drug container does not move as the septum piercing mechanism is transitioned from the unactivated configuration to the activated configuration.

In one embodiment, the septum piercing mechanism further includes a trigger block operatively associated with the needle support to prevent the needle support from moving towards the drug container in the unactivated configuration and a trigger lever operatively associated with the trigger block, the trigger lever being movable between first and second positions. Movement of the trigger lever from the first position to the second position enables the trigger block to move out of contact with the needle support so that the needle support can move towards the drug container.

In one embodiment, the trigger block and the needle support may include corresponding angled surfaces so that when the trigger lever is moved to the second position, the trigger block is moved with respect to the needle support enabling the needle support to move towards the drug container.

In one embodiment, the biasing member includes first and second torsion springs mounted on either side of the needle support. The first and second torsion springs may each include a first leg for bearing against an internal surface of the drug delivery device and a second leg for bearing against and biasing the needle support toward the drug container.

In one embodiment, the biasing member may be selected from one of a torsion spring, a leaf spring, and a conical spring. The biasing member may be positioned between the needle support and one or more interior portions of the drug delivery device.

In another embodiment, disclosed herein is a drug delivery device for administering a liquid drug stored in a drug container located within the drug delivery device to a patient. The drug delivery device may include a drug container, a needle insertion mechanism, a needle conduit, and a septum piercing mechanism. The drug container may include a liquid drug and a septum at one end of the drug container for sealing the liquid drug within the drug container. The needle insertion mechanism is adapted and configured for insertion into the patient for administering the liquid drug. The needle conduit may include a first end operatively associated with the drug container and a second end coupled to the needle insertion mechanism. The septum piercing mechanism is adapted and configured for piercing the septum of the drug container. The septum piercing mechanism may include a needle support operatively coupled with the first end of the needle conduit and a cam mechanism pivotably coupled to an interior portion of the drug delivery device.

In use, the septum piercing mechanism is movable between an unactivated configuration and an activated configuration via pivotable movement of the cam mechanism. In in the unactivated configuration, the first end of the needle conduit is separated from the liquid drug stored in the drug container via the septum. In the activated configuration, the first end of the needle conduit pierces through the septum so that the needle conduit is in fluid communication with the liquid drug stored in the drug container.

In one embodiment, the drug delivery device may further include a drive mechanism for moving the drug container from a first position to a second position, movement of the drug container from the first position to the second position transitions the septum piercing mechanism from the unactivated configuration to the activated configuration. Activation of the drive mechanism may transfer a force to a plunger associated with the drug container. In the unactivated configuration, the force to the plunger may move the drug container from the first position to the second position, in the activated configuration, the force to the plunger moves the plunger with respect to the drug container. Movement of the drug container from the first position to the second position may cause the drug container to contact the cam mechanism, in turn, causing the cam mechanism to pivot and move the needle support toward the drug container.

In one embodiment, the drug container may include a cap, the cap including the needle support positioned therein. The cam mechanism may be positioned between a top surface of the cap and an internal wall surface of the drug delivery device.

In the unactivated configuration, the top surface of the cap may be spaced a distance D1 away from the internal wall surface of the drug delivery device. In the activated configuration, the top surface of the cap may be spaced a distance D2 away from the internal wall surface of the drug delivery device, where the distance D2 is less than the distance D1.

In one embodiment, the cam mechanism may include first and second legs, each of the first and second legs may include first and second ends, the first ends of the first and second legs being operatively coupled to the cap of the drug container, the second ends of the first and second legs being operatively coupled to the needle support.

Movement of the drug container from the first position to the second position may cause the top surface of the cap to move the first and second legs of the cam mechanism causing the first and second legs to pivot about first and second pivot points, respectively, so that the second ends of the first and second legs of the cam mechanism move the needle support from the unactivated configuration to the activated configuration.

In one embodiment, the cam mechanism may include first and second links pivotably coupled to first and second protrusions, respectively, extending from an interior wall surface of the drug delivery device. Movement of the drug container from the first position to the second position may cause the cap to contact the first and second links causing the first and second links to rotate and thus causing the needle support to move from the unactivated configuration to the activated configuration.

BRIEF DESCRIPTION OF THE DRAWINGS

FIG. 6A illustrates a detailed, side view of a second example embodiment of a septum piercing mechanism in accordance with the disclosure, the septum piercing mechanism illustrated in a first or unactivated configuration;

FIG. 6B illustrates a cross-sectional view of the septum piercing mechanism shown in FIG. 6A taken along line 6B-6B in FIG. 6A;

FIG. 6C illustrates a cross-sectional view of the septum piercing mechanism shown in FIG. 6A taken along line 6C-6C in FIG. 6A rotated ninety-degrees;

FIG. 6D illustrates a detailed, side view of the septum piercing mechanism shown in FIG. 6A, the septum piercing mechanism illustrated in a second or activated configuration;

FIG. 6E illustrates a cross-sectional view of the septum piercing mechanism shown in FIG. 6D taken along line 6E-6E in FIG. 6D;

FIG. 6F illustrates a cross-sectional view of the septum piercing mechanism shown in FIG. 6D taken along line 6E-6E in FIG. 6D rotated ninety-degrees;

FIG. 8B illustrates a perspective detailed view of the septum piercing mechanism shown in FIG. 8A;

FIG. 8C illustrates a side detailed view of the septum piercing mechanism shown in FIG. 8A;

FIG. 8D illustrates an alternate detailed view of the septum piercing mechanism shown in FIG. 8A;

FIG. 13A illustrates a detailed, exploded, perspective view of a ninth example embodiment of a septum piercing mechanism in accordance with the disclosure;

FIG. 13B illustrates a detailed, exploded, side view of the septum piercing mechanism shown in FIG. 13A;

FIG. 13C illustrates a perspective, side view of an example embodiment of a conical spring member that may be used in combination with the septum piercing mechanism shown in FIG. 13A;

Figure 1:
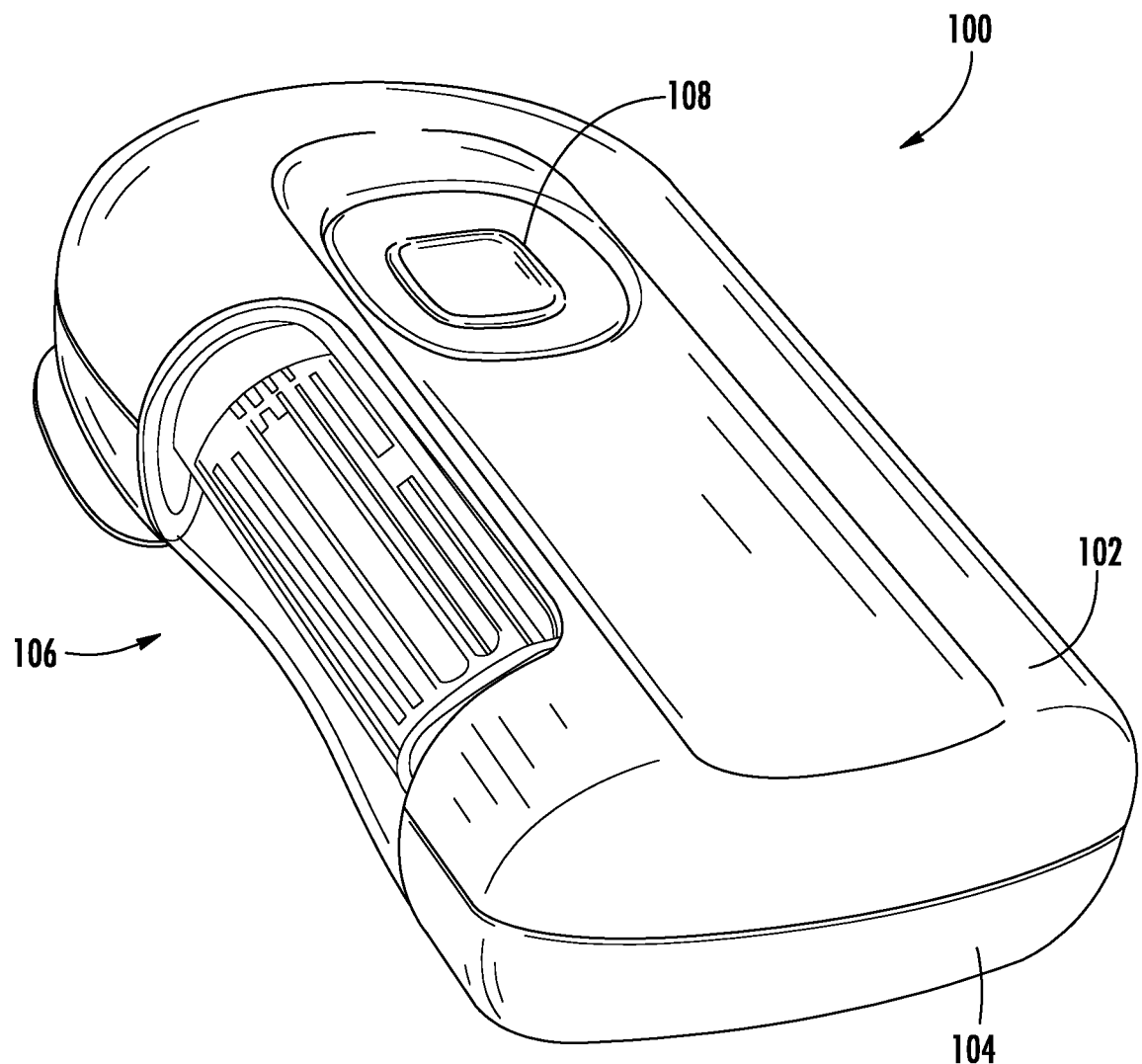
FIG. 1 is a top, perspective view of an example embodiment of a drug delivery device.

The drawings are not necessarily to scale. The drawings are merely representations, not intended to portray specific parameters of the disclosure. The drawings are intended to depict exemplary embodiments of the disclosure, and therefore are not be considered as limiting in scope. In the drawings, like numbering represents like elements.

DETAILED DESCRIPTION

Embodiments of various septum piercing mechanisms, systems, components, arrangements, and methods related to drug delivery devices in accordance with the present disclosure will now be described more fully hereinafter with reference to the accompanying drawings, in which preferred embodiments of the present disclosure are presented. In some embodiments, septum piercing mechanisms may be incorporated into a wearable drug delivery device. The septum piercing mechanisms of the present disclosure may, however, be embodied in many different forms and should not be construed as being limited to the embodiments set forth herein. Rather, these embodiments are provided so that this disclosure will convey certain example aspects of the septum piercing mechanisms to those skilled in the art. In the drawings, like numbers refer to like elements throughout unless otherwise noted.

In connection with drug delivery devices, for example, wearable drug delivery devices, it may be beneficial to keep the fluid path of the liquid drug separate from the liquid drug until the time the drug is administered to the patient. As such, in accordance with one aspect of the present disclosure, the drug delivery device may include a mechanism, system, arrangement, component, and/or method (collectively referred to herein as a septum piercing mechanism without the intent to limit) for moving the needle forming a portion of the fluid path through a septum or barrier or stopper (collectively referred to herein as a septum without the intent to limit) that seals a drug container or cartridge (collectively referred to herein as a container without the intent to limit) so that the needle can access the liquid drug within the drug container.

In one embodiment, the septum piercing mechanism may include a needle holder or support (collectively referred to herein as a needle support without the intent to limit). The needle support may be fixed in place (e.g., fixedly positioned, stationary), for example, when the drug delivery device is stored on the shelf or elsewhere. At the time of device activation, stored energy may be released to press and/or move the needle support toward the drug container, which, in turn, causes the needle to penetrate the septum of the drug container to place the fluid path in fluid communication with the liquid drug located within the container.

In various embodiments, the disclosed septum piercing mechanism addresses the issue of high loss of energy when using a drive system to pierce a container. That is, in one embodiment, the septum piercing mechanism employs a high force from the drive system, and converts a small movement, high force (e.g., a drive that moves the drug container towards the needle) into a large movement, low force (e.g., the needle is driven towards the drug container) through, for example, a cam or lever system or mechanism (collectively referring to herein as a cam mechanism without the intent to limit). By using a cam mechanism, it is possible to bring the needle towards the drug container at the same time that the drug container is being driven towards the needle. This means a smaller portion of the drive stroke is needed to pierce the septum of the drug container. This may be advantageous when the drive system uses stored energy such as, for example, in connection with a spring or other biasing member. When using a spring, the highest available force is at the start of motion, and force is reduced as the spring expands. By using a cam mechanism to reduce the amount of expansion, the drive spring must travel to pierce the septum of the drug container, the size of the drive spring can be reduced, thus providing for a smaller and lighter overall drug delivery device. Other advantages of incorporating a cam mechanism include incorporation of a smaller drive spring having a shorter stroke (e.g., minimize spring stroke, maximize energy efficiency), reducing drive impact on the drug container (e.g., energy is used to move a cam instead of accelerating the drug container), decreasing drug container movement required for the needle to pierce the septum, and protection of the needle during shipping.

Alternatively, as will be described in greater detail, various embodiments of the septum piercing mechanism may incorporate a biasing or spring member to drive the needle through the septum of the drug container. Such embodiments do not necessarily require a cam mechanism. In addition, such embodiments, may not require movement of the drug container. Advantages of incorporating the biasing or spring member include a shorter device length, decreasing or eliminating drug container movement required for the needle to pierce the septum, minimal handling of drug container thereby minimizing the risk to drug, decreased number of components, etc.

Figure 2:
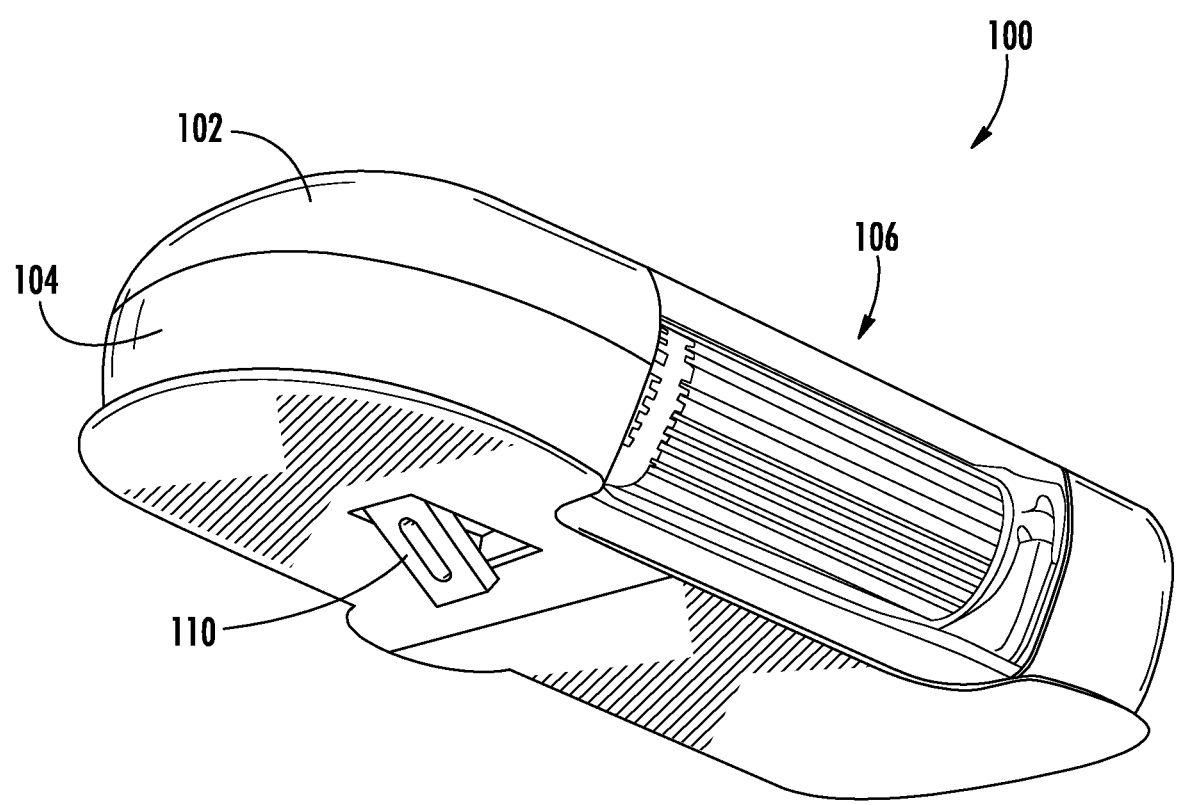
FIG. 2 is a bottom, perspective view of the drug delivery device shown in FIG. 1.

FIGS. 1 and 2 illustrate an embodiment of a drug delivery device 100. The drug delivery device 100 can include a top or upper portion 102 and a lower portion or base 104. The top portion 102 and the lower portion 104 can be coupled together to form a housing of the drug delivery device 100. The top portion 102 and the lower portion 104 can be coupled together to form an outside of the drug delivery device 100. Alternatively, it is envisioned that the housing may have other designs or form factors, and the present disclosure should not be so limited.

As illustrated the drug delivery device 100 may include an opening 106 for exposing a portion of a drug container positioned within the drug delivery device 100. The opening 106 can allow visual inspection and monitoring of the drug container. For example, the opening 106 enables a patient of the drug delivery device 100 to monitor an amount of liquid drug remaining in the drug container. In this way, a patient can monitor dosing status.

Additionally, the top portion 102 of the drug delivery device 100 may include a patient interaction element or component 108. In various embodiments, the patient interaction element 108 can be a push button or actuator. In use, the patient interaction element 108 can be used to activate the drug delivery device 100. For example, when a patient presses on the patient interaction element 108, the drug delivery device 100 can begin delivering the stored liquid drug from the drug container to the patient.

The drug delivery device 100 may also include an on-body interlock 110. The on-body interlock 110 may operate as a safety mechanism or actuator requiring actuation for the drug delivery device 100 to operate. In one embodiment, referring to FIG. 2, the on-body interlock 110 may extend from a lower surface of the lower portion or base 104, although it is envisioned that the on-body interlock 110 may extend from any portion of the housing. The on-body interlock 110 may be a button or switch that can retract into the drug delivery device 100 when the lower portion 104 is pressed or coupled to the patient. In use, the on-body interlock device 110 can be required to be depressed (e.g., passively) before the drug delivery device 100 can be activated. For example, when the drug delivery device 100 is coupled to a patient (e.g., pressed against the user's body), the on-body interlock device 110 can be passively depressed. Once depressed, the patient interaction element 108 can be subsequently used to activate the drug delivery device 100. Prior to the on-body interlock 110 being depressed, the patient interaction element 108 may be disengaged such that manipulation of the patient interaction element 108 does not activate the drug delivery device 100. The on-body interlock 110 may also operate to stop or cease operation of the drug delivery device 100.

Figure 3:
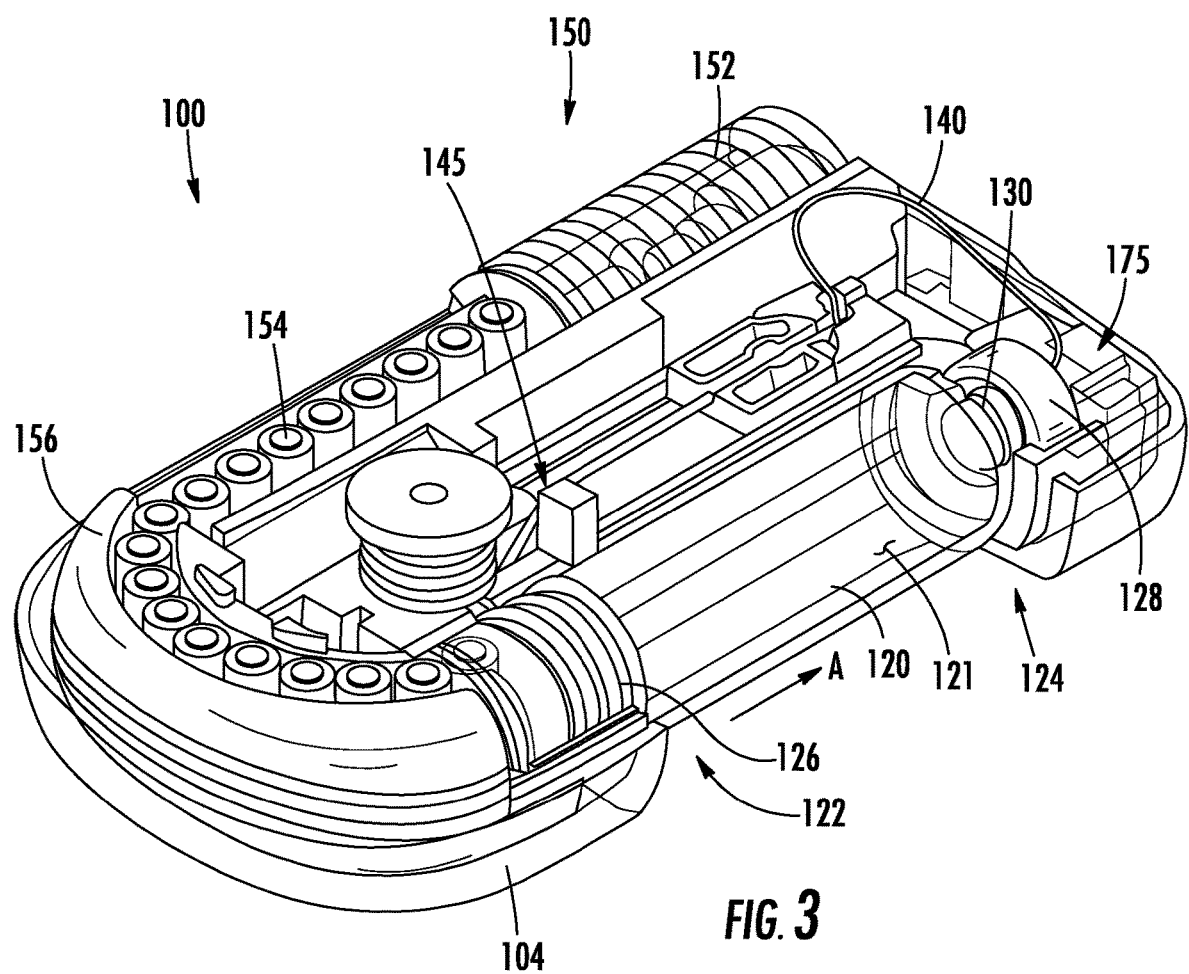
FIG. 3 is a top, perspective view of the drug delivery device shown in FIG. 1 with a cover portion removed.
Figure 4:
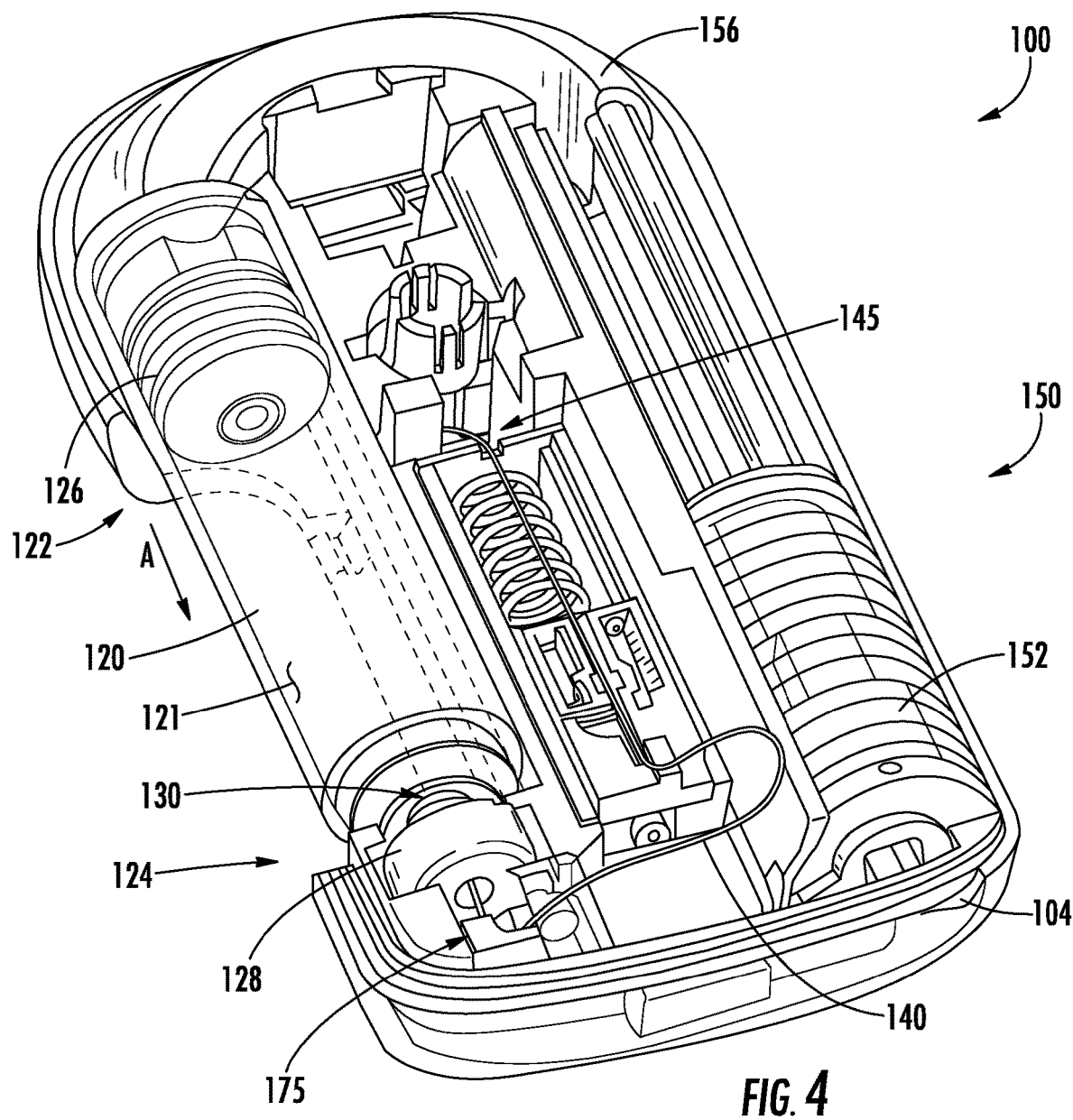
FIG. 4 is an alternate top, perspective view of the drug delivery device shown in FIG. 1 with a cover portion removed.

FIGS. 3 and 4 illustrate a first exemplary arrangement of internal components of the drug delivery device 100. The drug delivery device 100 may include a drug container 120. The drug container 120 may include a first end 122 and a second end 124. The drug container 120 may be sealed at or near the first end 122 and the second end 124. The first end 122 may include a plunger 126. The second end 124 may include a neck (e.g., a reduced diameter neck), a cap 128, and a septum 130 associated with the neck and cap 128. A liquid drug 121 may be contained within the drug container 120 between, for example, a sealing arrangement, including the septum 130, provided at the second end 124 of the drug container 120 and the plunger 126. The drug container 120 of the drug delivery device 100 may be, for example, an ISO standardized drug cartridge. The drug container 120 may be formed from any suitable material including, for example, glass, plastic, etc. The plunger 126 may be formed from any suitable material including, for example, a plastic material such as, for example, an elastomeric polymer material.

In use, the liquid drug 121 contained within the drug container 120 may be accessed through the second end 124 of the drug container 120. A drug container septum piercing mechanism 175 may be positioned at or near the second end 124 for accessing the liquid drug 121. The septum piercing mechanism 175 may enable access to the liquid drug 121 by piercing through the septum 130 when activated. That is, in use, and as will be described in greater detail below, the septum piercing mechanism 175 may include or be associated with a needle or other component to pierce the septum 130 to access the liquid drug 121. The septum piercing mechanism may be movable between a first or unactivated configuration or state, and a second or activated configuration or state. In the first or unactivated configuration or state (e.g., prior to piercing the septum 130), the septum 130 may be unpierced leaving the liquid drug 121 inaccessible and sealed within the drug container 120. The septum piercing mechanism 175 may remain in an idle state prior to being activated to access the liquid drug 121. In the second or activated configuration or state (e.g., after activation of the septum piercing mechanism 175), the needle may extend through the septum 130 so that the liquid drug 121 contained within the drug container 120 is now in fluid communication.

That is, the septum piercing mechanism 175 can couple or place the liquid drug 121 located in the drug container 120 in fluid communication with a needle conduit 140 located in the drug delivery device 100. The needle conduit 140 may include tubing for providing a path for a portion of the liquid drug 121 that is expelled from the drug container 120. In various embodiments, the needle used to pierce the septum 130 can be a part of the needle conduit 140 as opposed to a portion of the septum piercing mechanism 175. The needle conduit 140 may be formed from any suitable material including, for example, plastic tubing, metal tubing, etc.

In various embodiments, the septum piercing mechanism 175 may be positioned at or near the second end 124 along with the needle conduit 140. Thus, the liquid drug 121 stored in the drug container 120 can be accessed through the septum piercing mechanism 175 without having to move the drug container 120.

The needle conduit 140 can route the liquid drug 121 from the drug container 120 to a needle insertion mechanism or component 145. The needle insertion mechanism or component 145 can provide an entry point to a patient. The needle insertion mechanism or component 145 can be any suitable needle including, for example, a hard needle, a soft needle, a cannula, etc. that provides access to the patient such that the liquid drug 121 can be delivered to the patient.

As illustrated, the drug delivery device 100 may also include a drive mechanism 150 for expelling the liquid drug 121 from the drug container 120. For example, the drive mechanism 150 may include a drive spring 152, and one or more force transfer elements 154. In use, the drive spring 152 may apply a force that can be applied to the force transfer elements 154. The force transfer elements 154 can be arranged to transfer the force from the drive spring 152 to various other components including, for example, the plunger 126 and/or septum piercing mechanism 175 for piercing the septum 130. That is, for example, in one embodiment, when the force from the drive spring 152 is applied to the septum piercing mechanism 175, a needle associate with the septum piercing mechanism 175 can advance through the septum 130, as will be described in greater detail below. As the needle advances through the septum 130, the liquid drug 121 within the drug container 120 can be forced out of the drug container 120 into the needle conduit 140 and on to the needle insertion mechanism or component 145 for delivery to the patient.

The force transfer elements 154 can be formed of any suitable material including, for example, glass, metal (e.g., stainless steel), a polymer or other plastic, etc. and can be provided in numerous different forms or configurations. The drive spring 152 can be any type of spring. The drive spring 152 can have any desired spring constant value, k. The drive spring 152 is not limited to a single spring and can include one or more springs. In various embodiments, the drive spring 152 can include one or more compression springs and/or torsion springs. For example, the drive spring 152 can include one or more linear compression springs arranged in a parallel arrangement, a series arrangement, an arrangement of nested springs in series, or any combination thereof. In various embodiments, the drive spring 152 can be implemented as double series springs.

The drive spring 152 can be coupled to the force transfer elements 154 by any suitable means now known or hereafter developed including, for example, via compressive forces.

Alternatively, the drive spring 152 can be coupled to the force transfer elements 154 via, for example, welding, adhesive, fasteners, etc. In various embodiments, the drive spring 152 can include a fixed component or plate coupled to an end of the drive spring 152. The fixed component can have a width that is substantially the same as the width of the coils of the drive spring 152. The fixed component can be substantially flat and can be directly coupled to the force transfer elements 154.

The drug delivery device 100, for example, the bottom portion 104 can include a track 156 for guiding the force transfer elements 154. The track 156 can be a guide, a tube, a housing or combinations thereof. In various embodiments, the drive spring 152 and the force transfer elements 154 can be positioned within the track 156. The track 156 can surround or cover the force transfer elements 154. The track 156 can be formed of any suitable material including, for example, a plastic material, a metal (e.g., stainless steel), any combination thereof, etc. For example, an outer portion of the curved portion of the track 156 may be formed of a metal while an inner portion of the curved portion of the track 156 may before formed of a hard plastic. The track 156 can form any shape and can be arranged to take on any shape to guide the force transfer elements 154 from the drive spring 154 toward the drug container 120.

The drug delivery device 100 is merely an example embodiment. The septum piercing mechanism of the present disclosure may be used in combination with other drug delivery devices.

Figure 5A:
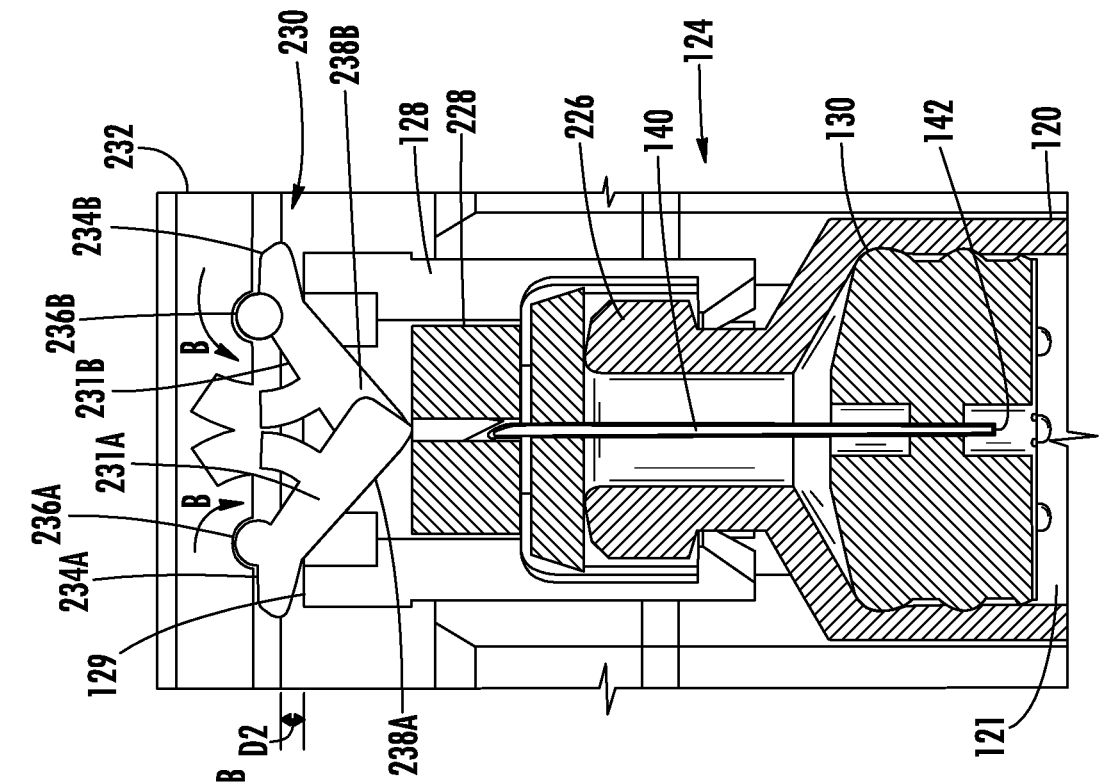
FIG. 5A is a detailed, cross-sectional view of a first example embodiment of a septum piercing mechanism in accordance with the disclosure, the septum piercing mechanism illustrated in a first or unactivated configuration.
Figure 5B:
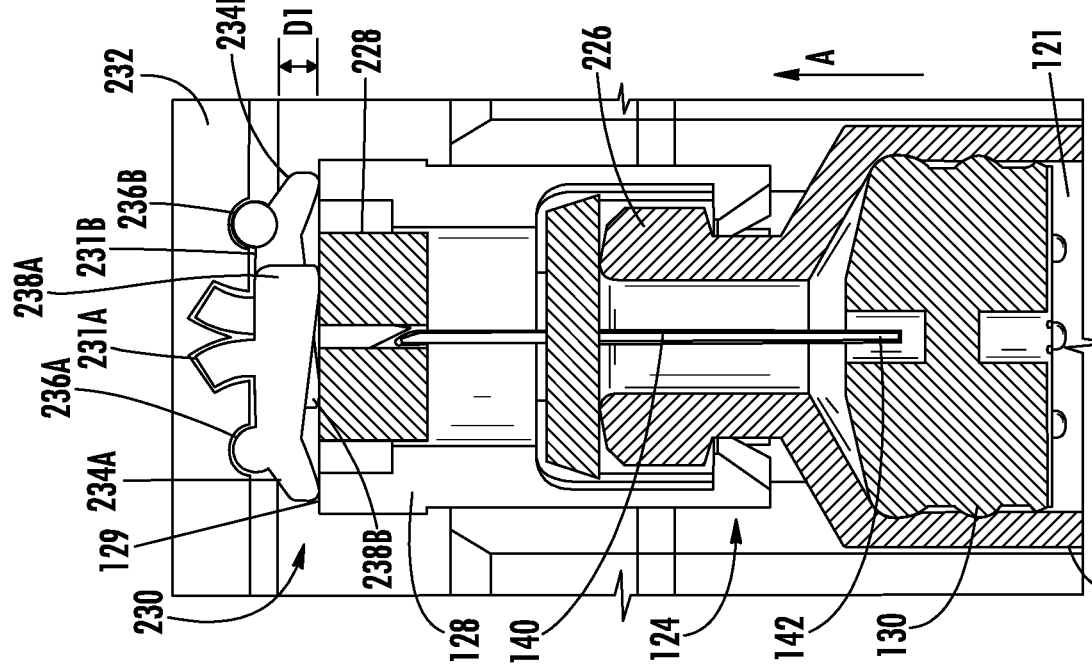
FIG. 5B is a detailed, cross-sectional view of the septum piercing mechanism shown in FIG. 5A, the septum piercing mechanism illustrated in a second or activated configuration.

FIGS. 5A and 5B illustrate a first example embodiment of a septum piercing mechanism in accordance with the present disclosure. As previously mentioned, in its first or unactivated configuration (FIG. 5A), before the drug delivery device 100 is activated to delivery liquid drug 121 to the patient, the needle conduit 140 is not be in fluid communication with the liquid drug 121 in the drug container 120. Thus, upon activation of the drug delivery device 100, the drive mechanism 150, for example, the drive spring 152, may apply a force to the force transfer element 154, which, in turn, may transfer the force to the plunger 126. Because the needle conduit 140 is not yet coupled to the liquid drug 121, and because the liquid drug 121 is incompressible, the force applied to the plunger 126 will move the entire drug container 120 in the direction of arrow "A". Movement of the drug container 120 can cause an end 142 of the needle conduit 140 to pierce a septum 130 that is positioned near, for example, the second end 124 of the drug container 120. Upon piercing the septum 130, the end 142 of the needle conduit 140 will be exposed to (e.g., in fluid communication with) the liquid drug 121 within the drug container 120 and further movement of the plunger 126 will cause the liquid drug 121 to be expelled through the needle conduit 140.

FIG. 5A shows the septum piercing mechanism 175 in a first or unactivated configuration such that the end 142 of the needle conduit 140 is separated (e.g., blocked, not in fluid communication) from the liquid drug 121 in the drug container 120 by the septum 130. Upon activation of the drug delivery device 100, the drive mechanism 150 (e.g., the drive spring 152 and the force transfer element 154) apply a force to the plunger 126, which causes the drug container 120 to move in the direction of arrow "A".

As previously described, a cap 128 may be coupled to the second end 124 of the drug container 120. The cap 128 may be coupled to the drug container 120 by any suitable means now known or hereafter developed. For example, in one embodiment, the cap 128 may be coupled to a mouth portion 226 of the drug container 120. The cap 128 may include or be operatively associated with a needle support 228 and a cam mechanism 230. In use, the cam mechanism 230 may be any device or mechanism for moving the needle conduit 140 through the septum 130 and into fluid communication with the liquid drug 121. In one embodiment, the cam mechanism 230 may be a dual cam mechanism that contacts the needle support 228 associated with the cap 128, pressing or moving the needle support 228 and the needle conduit 140 toward the drug container 120 until the end 142 of the needle conduit 140 pierces the septum 130.

The needle support 228 may be entirely contained within the cap 128, with the cam mechanism 230 positioned between a top surface 129 of the cap 128 and an internal wall 232 of the drug delivery device 100. In the first or unactivated configuration, the top surface 129 of the cap 128 is spaced a distance D1 away from the internal wall 232 of the drug delivery device 100.

The cam mechanism 230 may include first and second legs 231A, 231B. Each of the first and second legs 231A, 231B may include first and second ends 234A, 234B, 238A, 238B, respectively. In use, as the drug container 120 moves in the direction of arrow "A" as previously described, the top surface 129 of the cap 128 contacts or presses against the first ends 234A, 234B of the first and second legs 231A, 231B, respectively, which in turn causes the first and second legs 231A, 231B to pivot about first and second pivot points or axes 236A, 236B so the first and second legs 231A, 231B rotate as illustrated by arrows "B" (FIG. 5B). Rotation of the first and second legs 231A, 231B causes the second ends 238A, 238B of the first and second legs 231A, 231B to contact the needle support 228 associated with the cap 128, pressing or moving the needle support 228 and the needle conduit 140 toward the drug container 120 until the end 142 of the needle conduit 140 pierces the septum 130. This second or activated configuration is shown in FIG. 5B. In the second or activated configuration, the top surface 129 of the cap 128 is now spaced a distance D2 away from the wall 232 of the drug delivery device 100, where the distance D2 is less than the distance D1. In this second or activated configuration, the end 142 of the needle conduit 140 is exposed to (e.g., in fluid communication with) the liquid drug 121 in the drug container 120 so that as force continues to be applied to the plunger 126, the liquid drug 121 is expelled from the drug container 120 through the needle conduit 140. In one example embodiment, approximately 0.5 mm movement of the drug container 120 may result in approximately 3 mm of needle movement.

FIGS. 6A-6F illustrate a second example embodiment of a septum piercing mechanism in accordance with the disclosure. Elements of this embodiment are substantially the same as the elements described above in relation to the first example embodiment described and illustrated in connection with FIGS. 5A and 5B, with the exception that in connection with the present embodiment, the cam mechanism 330 may include first and second links 342A, 342B. In use, the first and second links 342A, 342B may be straight and pivotably coupled to cam protrusions 344A, 344B extending from, for example, an interior wall 232 of the drug delivery device 100. FIGS. 6A-6C illustrate the septum piercing mechanism in a first or unactivated configuration in which the end 142 of the needle conduit 140 is separated from (e.g., blocked, not in fluid communication with) the liquid drug 121 in the drug container 120 by the septum 130. FIGS. 6D-6F illustrate the septum piercing mechanism in a second or activated configuration in which the end 142 of the needle conduit 140 is exposed to (e.g., in fluid communication with) the liquid drug 121 within the drug container 120.

In use, movement of the drug container 120 causes resulting movement of the cap 128. In turn, the cap 128 pushes on the cam links 342A, 342B, causing the cam links 342A, 342B to rotate resulting in the cam links 342A, 342B pushing on the needle support 228 and thus pushing the needle 140 through the septum 130 and into fluid communication with the liquid drug 121 located in the drug container 120. That is, movement of the cap 128 pushes against first ends of the cam links 342A, 342B, which, in turn, causes the cam links 342A, 342B to rotate resulting in second ends of the cam links 342A, 342B pushing on the needle support 228 and thus pushing the needle 140 through the septum 130 and into fluid communication with the liquid drug 121 located in the drug container 120. Rotation of the cam mechanism 330 (e.g., straight cam links 342A, 342B) may be caused by their engagement with the top surface 129 of the cap 128. As the cam links 342A, 342B rotate, they contact the needle support 228, and cause the end 142 of the needle conduit 140 to pierce the septum 130.

Figure 7:
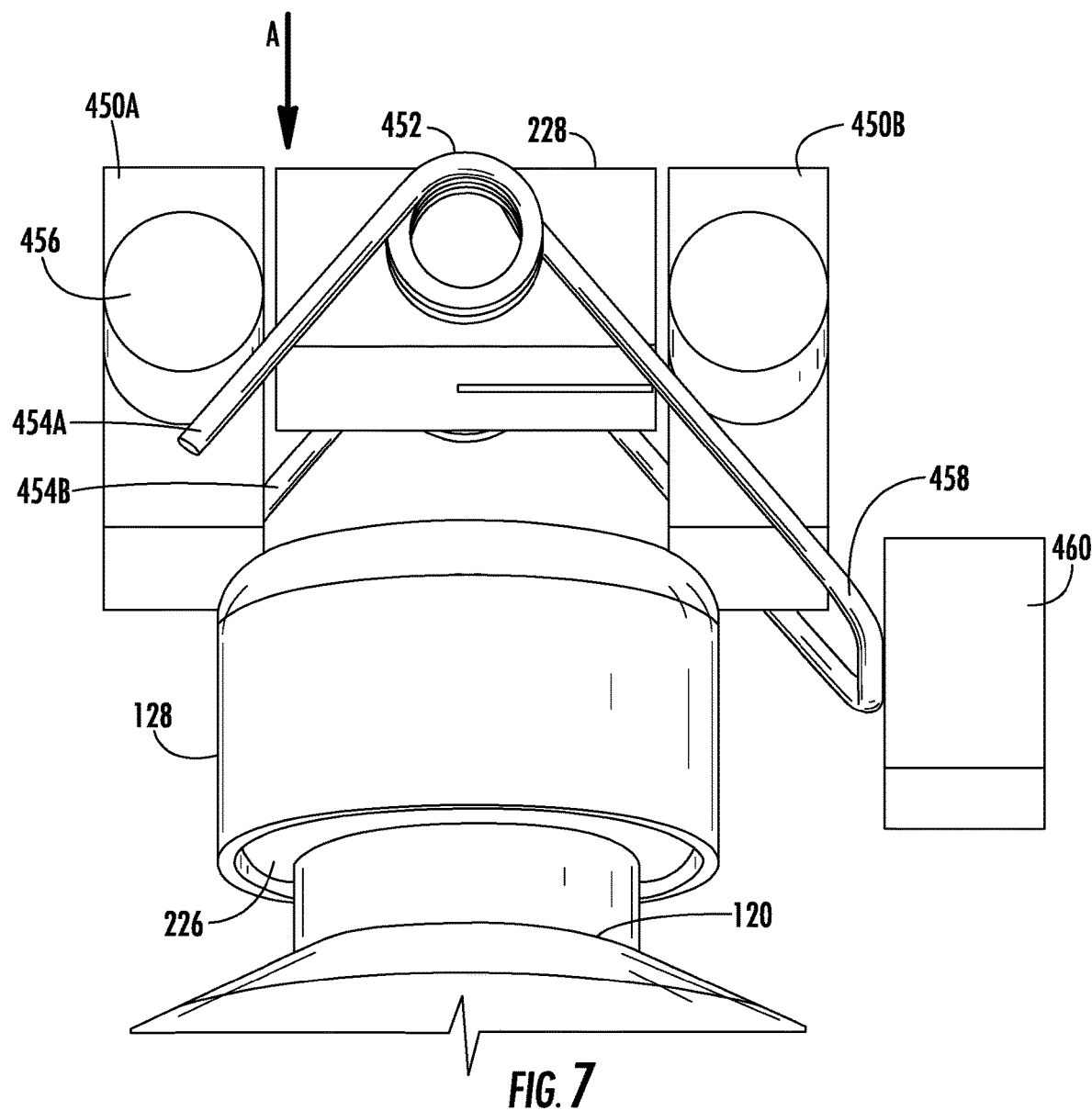
FIG. 7 illustrates a detailed view of a third example embodiment of a septum piercing mechanism in accordance with the disclosure.
Figure 8A:
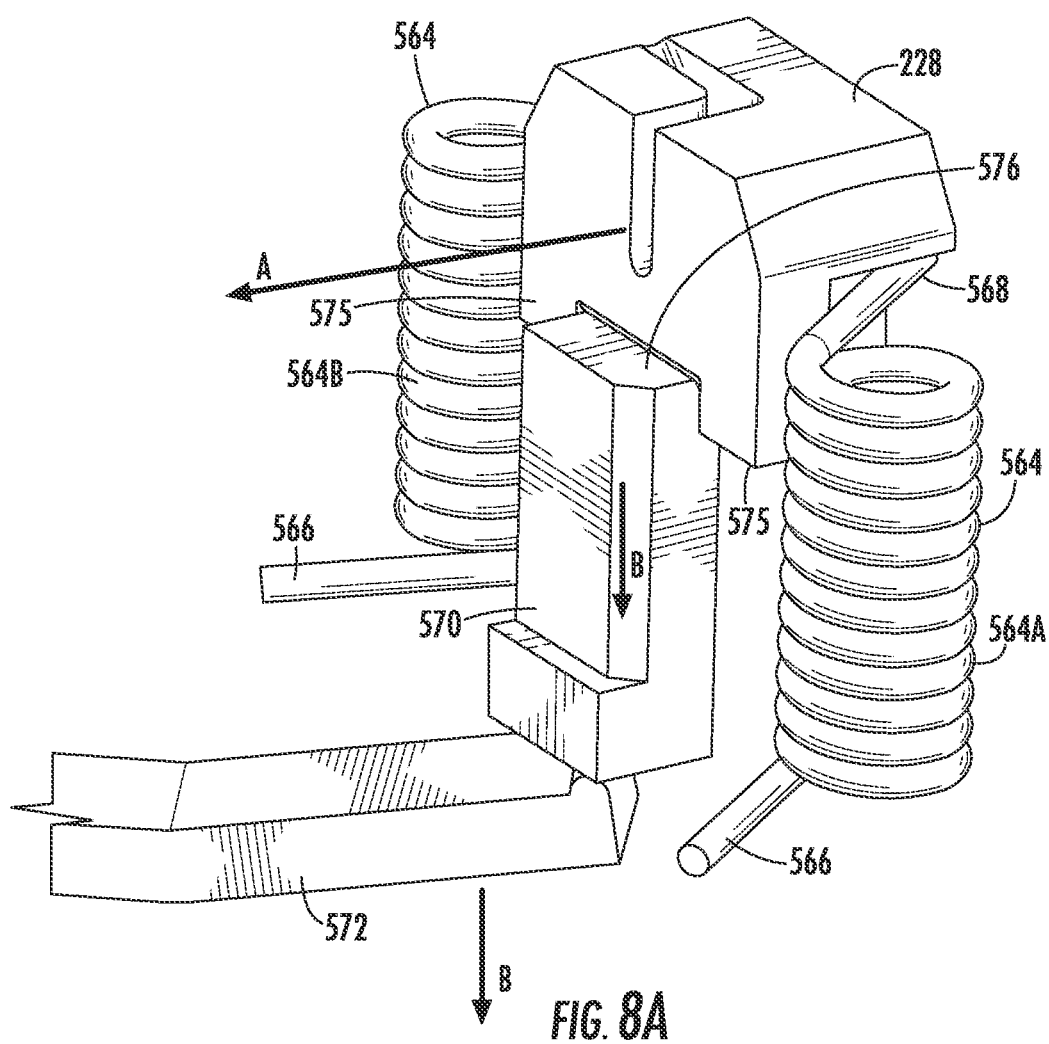
FIG. 8A illustrates a detailed view of a fourth example embodiment of a septum piercing mechanism in accordance with the disclosure.

FIG. 7 illustrates a third example embodiment of a septum piercing mechanism in accordance with the disclosure. In this embodiment, the drug container 120 may remain fixedly positioned (e.g., stationary). That is, in use, the drug container 120 is not required to move for the end 142 of the needle conduit 140 to pierce the septum 130 to expose or place the needle conduit 140 in fluid communication with the liquid drug 121 in the drug container 120. One advantage of this arrangement is that it may reduce the overall length of the drug delivery device 100. Another advantage is that the drug delivery device 100 may also contain fewer parts to implement. For ease of explanation, the needle conduit 140 and septum 130 have been removed for clarity, though it will be understood how they may interact in a working device such that in a first or unactivated configuration, the end 142 of the needle conduit 140 is separated from (e.g., not in fluid communication with) the liquid drug 121 in the drug container 120 via the septum 130 and in the second or activated configuration, the end 142 of the needle conduit 140 is moved through the septum 130 to expose the needle conduit 140 to the liquid drug 121 (e.g., the end 142 of the needle conduit 140 is moved into fluid communication with the liquid drug 121).

As illustrated in FIG. 7, the septum piercing mechanism may be positioned (e.g., mounted) adjacent to the cap 128 disposed on a mouth portion 226 of the drug container 120, as previously described. First and second bearing blocks 450A, 450B may be disposed on opposite sides of the needle support 228. The septum piercing mechanism may include a biasing or spring member, 452. The biasing or spring member 452 may be, for example but not limited to, a double body torsion spring operatively associated with (e.g., mounted to) the needle support 228. The spring (e.g., double body torsion spring) 452 may include first and second legs 454A, 454B bearing against protrusions 456 disposed on opposite sides of the first bearing block 450A. A loop end 458 of the spring (e.g., double body torsion spring) 452 may bear against a wall portion 460 of the drug delivery device 100. In the first or unactivated configuration or state, the spring (e.g., double body torsion spring) 452 may be compressed between the protrusions 456 and the wall portion 460 of the drug delivery device 100, which causes a force to be applied to the needle support 228 tending to move the needle support 228, and hence the needle conduit 140, toward the drug container 120. However, in the first or unactivated configuration, the needle support 228 may be supported in a manner that prevents it from moving toward the drug container 120 until the drug delivery device 100 is activated. When the drug delivery device 100 is activated, the needle support 228 can move in the direction of arrow "A", under the force of the spring (e.g., double body torsion spring) 452 toward the drug container 120 until the end 142 of the needle conduit 140 pierces the septum 130 placing the end 142 of the needle 140 in fluid communication with the liquid drug 121 in the drug container 120.

FIGS. 8A-8D illustrate a fourth example embodiment of a septum piercing mechanism in accordance with the present disclosure. For ease of explanation, the drug container 120, the needle conduit 140, the septum 130, and other components may have been removed from some of the figures for clarity, though it will be understood how they may interact in a working device such that in a first or unactivated configuration, the end 142 of the needle conduit 140 is separated from (e.g., not in fluid communication with) the liquid drug 121 in the drug container 120 via the septum 130 and in the second or activated configuration, the end 142 of the needle conduit 140 is moved through the septum 130 to expose the needle conduit 140 to the liquid drug 121 (e.g., the end 142 of the needle conduit 140 is moved into fluid communication with the liquid drug 121). In connection with the present embodiment, the drug container 120 may be fixedly positioned (e.g., stationary). That is, similar to the embodiment of FIG. 7, the drug container 120 is not required to move for the end 142 of the needle conduit 140 to pierce the septum 130 to expose the needle conduit 140 to the liquid drug 121 within the drug container 120.

As mentioned, the needle support 228 may be positioned (e.g., mounted) adjacent to the cap 128 disposed on a mouth portion 226 of the drug container 120, as previously described. In some embodiments, the needle support 228 may include a set of legs 575 straddling a second end surface 576 of a trigger block 570, wherein the set of legs 575 extend within a corresponding set of channels 577 of an internal wall 578 of the septum piercing mechanism. The septum piercing mechanism may include a biasing or spring member 564. The biasing or spring member 564 may be, for example, but not limited to, first and second torsion springs 564A, 564B mounted on either side of the needle support 228. The first and second torsion springs 564A, 564B) may each include first and second legs 566, 568. In use, the first legs 566 of the first and second torsion springs 564A, 564B may bear against internal surfaces of the drug delivery device 100. Meanwhile, the second legs 568 of the first and second torsion springs 564A, 564B may bear against and bias the needle support 228 in a direction toward the drug container 120 (arrow "A").

The septum piercing mechanism may also include the trigger block 570 for contacting the needle support 228 to prevent the needle support 228, and hence the needle conduit 140, from moving towards the drug delivery device 100 until the drug delivery device 100 is activated. The trigger block 570, in turn, may be supported by a trigger lever 572, and the trigger lever 572 may be coupled to a user-activated or automatically activated trigger mechanism (not shown). The trigger block 570 and the needle support 228 may be operatively associated with each other in any suitable manner that enables the trigger block 570 to resist movement of the needle support 228 until activated. For example, in one embodiment, the trigger block 570 and the needle support 228 may contact each other via correspondingly angled surfaces so that when the trigger lever 572 is moved in the direction of arrow "B" (e.g., when the drug delivery device 100 is activated), the force of the spring 564 (e.g., first and second torsion springs 564A, 564B) (directed in the direction of arrow "A") causes the needle support 228 to move in the direction of arrow "A", forcing the trigger block 570 to move in the direction of arrow "B". That is, movement of the trigger lever 572 enables movement of the trigger block 570 in the direction of arrow "B". As such, due to the corresponding angled surfaces and the forces supplied by the spring 564 (e.g., first and second torsion springs 564A, 564B), the needle support 228 is permitted to move in the direction of arrow "A", toward the drug container 120 until the end 142 of the needle conduit 140 pierces the septum 130 in the drug container 120, thus exposing the needle conduit 140 to the liquid drug 121 in the drug container 120.

As will be appreciated, other mechanism or manners for moving the trigger block with respect to the needle support may be used. For example, the trigger block 570 may be operatively associated with a biasing member or a spring of its own such that activation of the drug delivery device 100 and hence movement of the trigger lever 572 biases the trigger lever 572 in the direction of arrow "B" and out of contact with the needle support 228, thus enabling the needle support 228 to move in the direction of arrow "A", toward the drug container 120 until the end 142 of the needle conduit 140 pierces the septum 130 in the drug container 120. As will be appreciated, the trigger mechanism, including the trigger block 570 and the trigger lever 572, can be implemented in the embodiment of the septum piercing mechanism disclosed in connection with FIG. 7.

FIGS. 9A-14B illustrate various alternative embodiments of septum piercing mechanisms according to the present disclosure. Each of these septum piercing mechanisms are variously illustrated without one or more components, for example, the needle conduit 140, for the sake of clarity. It should be understood that the needle support 228 of these embodiments would be positioned (e.g., mounted) in similar fashion to the needle support 228 previously described. In addition, with the embodiments of FIGS. 9A-14B, the drug container 120 may remain fixedly positioned or stationary (e.g., the drug container 120 is not required to move for the end 142 of the needle conduit 140 to pierce the septum 130 to expose the needle conduit 140 to the liquid drug 121 in the drug container 120). Thus, in a first or unactivated configuration or state, the end 142 of the needle conduit 140 is separated from (e.g., the end 142 of the needle conduit 140 is not in fluid communication with) the liquid drug 121 in the drug container 120 via the septum 130 and in the second or activated configuration or state, the end 142 of the needle conduit 140 is moved through the septum 130 to expose the needle conduit 140 to the liquid drug 121 (e.g., to place the end 142 of the needle conduit 140 in fluid communication with the liquid drug 121). In addition, as will be appreciated, the trigger mechanism of FIGS. 8A-8D (including the trigger block 570 and the trigger lever 572), can be implemented in any/all of the embodiments disclosed in relation to FIGS. 9A-14B.

Figure 9A:
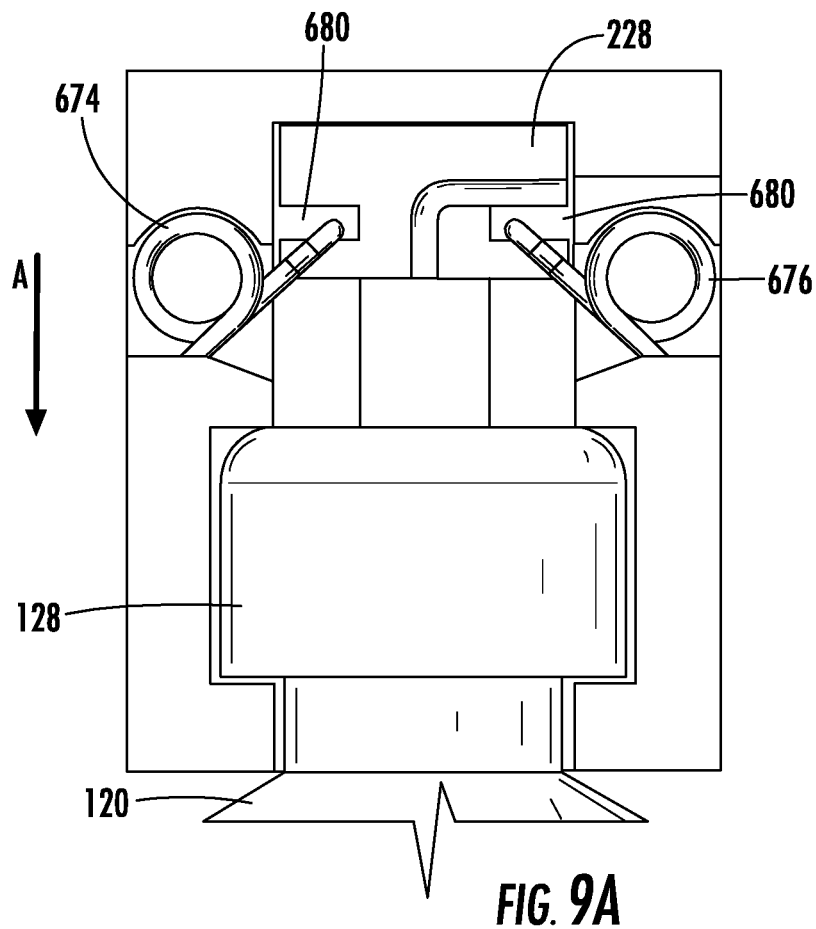
FIG. 9A illustrates a detailed, top view of a fifth example embodiment of a septum piercing mechanism in accordance with the disclosure.
Figure 9B:
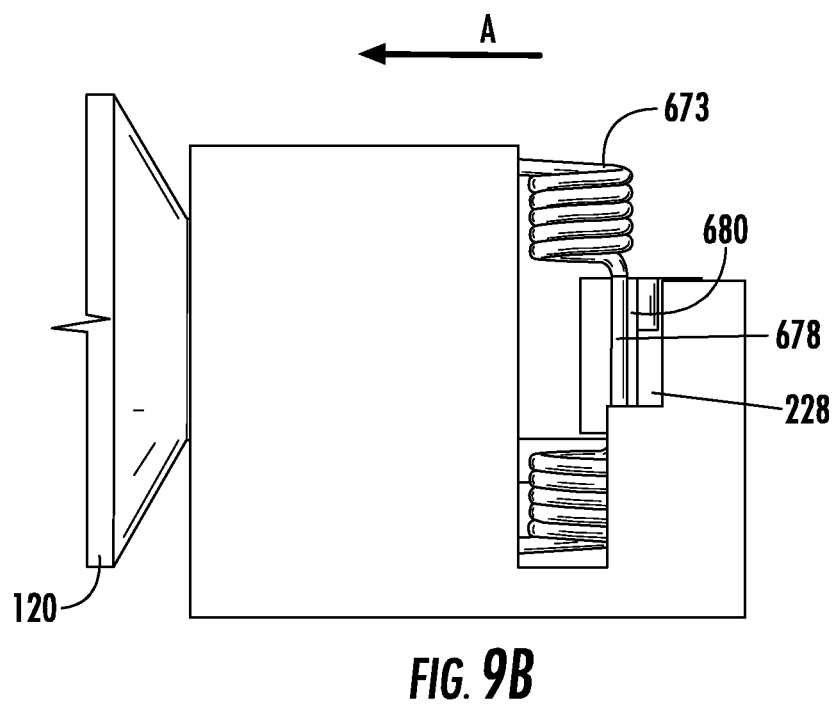
FIG. 9B illustrates a detailed, side view of the septum piercing mechanism shown in FIG. 9A.

FIGS. 9A and 9B illustrate a fifth example embodiment of a septum piercing mechanism in accordance with the disclosure. Similar to the fourth example embodiment illustrated in connection with FIGS. 8A-8D, in this embodiment, the needle support 228 is biased toward the drug container 120 in the direction of arrow "A" via a biasing or spring member 673. The biasing or spring member 673 may be, for example, but not limited to a double body torsion spring having portions 674, 676 that are connected to each other via a center portion or leg 678 which may be positioned in a slot 680 formed in the needle support 228. Thus, in a first or unactivated configuration or state, the end 142 of the needle conduit 140 is separated from the liquid drug 121 in the drug container 120 via a septum 130, as previously described, and in the second or activated configuration or state, the end 142 of the needle conduit 140 is moved in the direction of arrow "A" due to the force supplied to the needle support 228 by the spring (e.g., double body torsion spring) 673 to pierce the septum 130 to expose the needle conduit 140 to the liquid drug 121. As shown, the needle conduit 140 may be positioned behind the tongue of the spring (e.g., double body torsion spring) 673 and move between the first and second spring bodies. Incorporation of double body torsion springs 673 assists in maintaining the forces generally in line with the force of the needle insertion to minimize any moment. As such, the double body torsion springs 673 enables the end 142 of the needle conduit 140 to come out flatter in contrast to use of, for example, first and second torsion springs, which enable the end 142 of the needle conduit 140 to come out of the needle support at an angle.

Figure 10A:
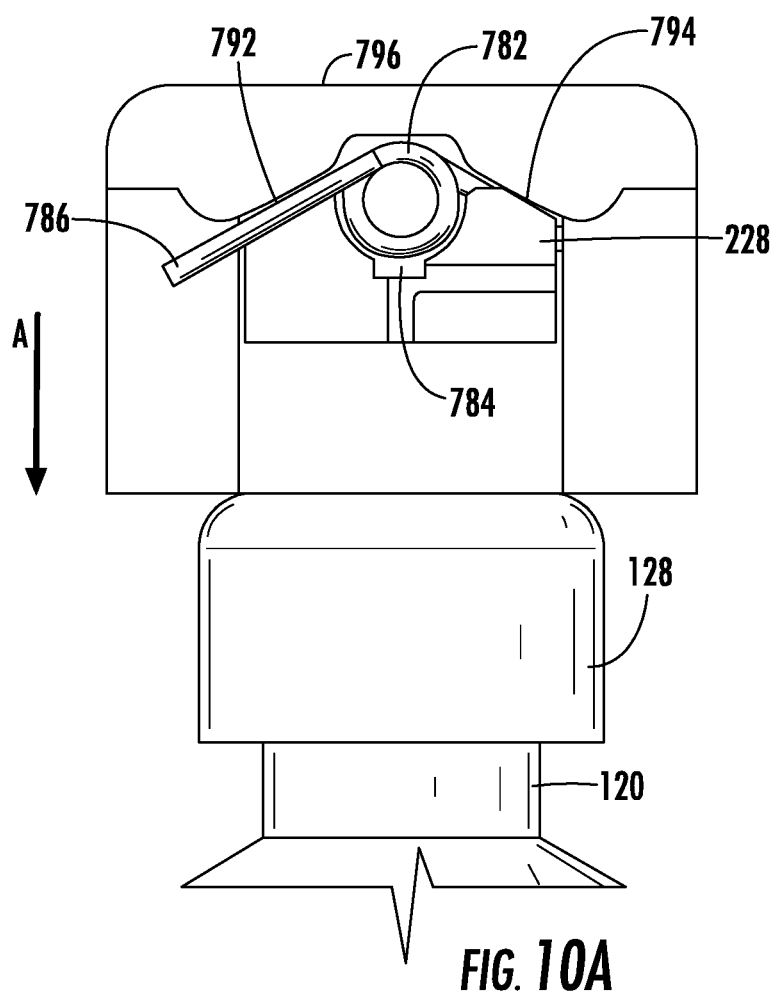
FIG. 10A illustrates a detailed, top view of a sixth example embodiment of a septum piercing mechanism in accordance with the disclosure.
Figure 10B:
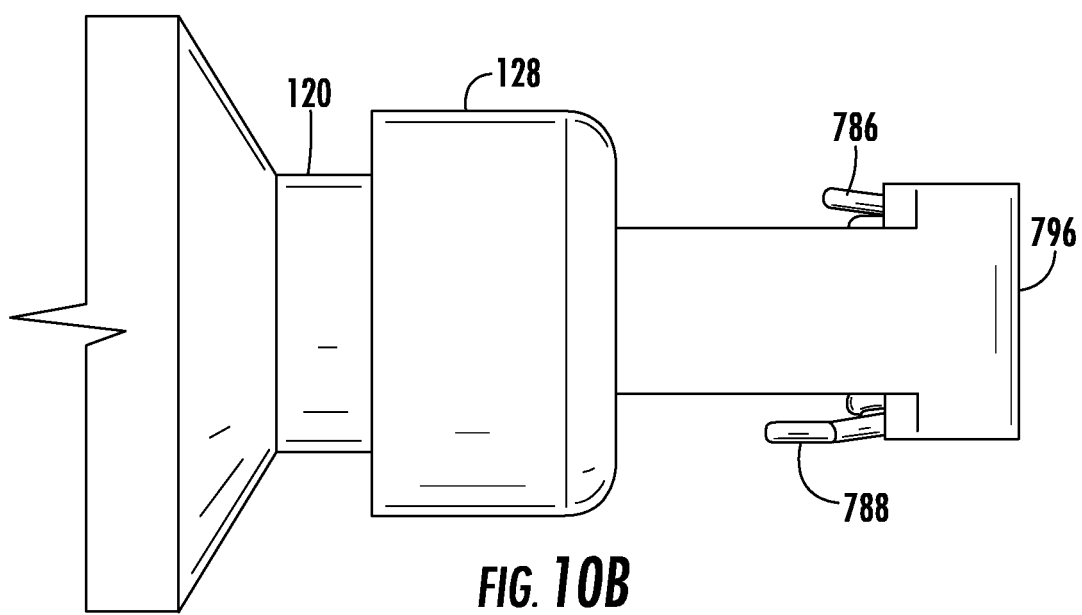
FIG. 10B illustrates a detailed, side view of the septum piercing mechanism shown in FIG. 10A.

FIGS. 10A and 10B illustrate a sixth example embodiment of a septum piercing mechanism in accordance with the disclosure. In this embodiment, the needle support 228 is biased toward the drug container 120 in the direction of arrow "A" via a biasing or spring member 782. The biasing or spring member 782 may be, for example, but not limited to, a single torsion spring 782 which may reside within a groove 784 formed in the needle support 228. The spring (e.g., torsion spring) 782 may include first and second legs 786, 788, which may bear against a pair of trust points 792, 794, respectively, coupled to an internal wall 796 of the drug delivery device 100. In a first or unactivated configuration or state, the end 142 of the needle conduit 140 is separated from the liquid drug 121 in the drug container 120 via the septum 130, as previously described, and in the second or activated configuration or state, the end 142 of the needle conduit 140 is moved in the direction of arrow "A" due to the force supplied to the needle support 228 by the spring (e.g., torsion spring) 782 to pierce the septum 130 to expose the needle conduit 140 to the liquid drug 121.

Figure 11A:
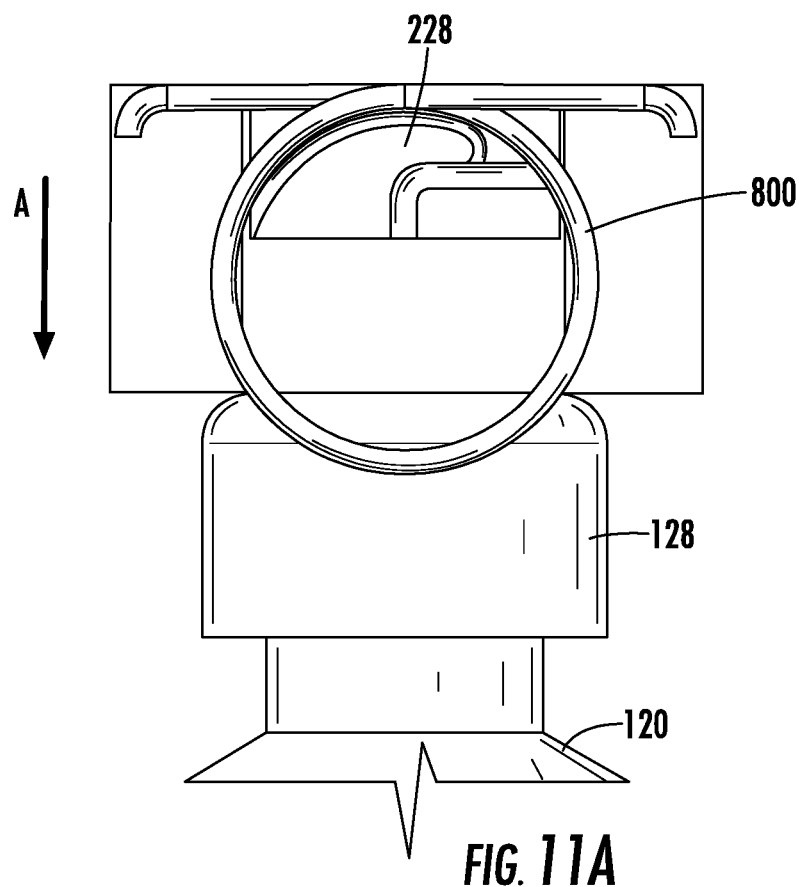
FIG. 11A illustrates a detailed, top view of a seventh example embodiment of a septum piercing mechanism in accordance with the disclosure.
Figure 11B:
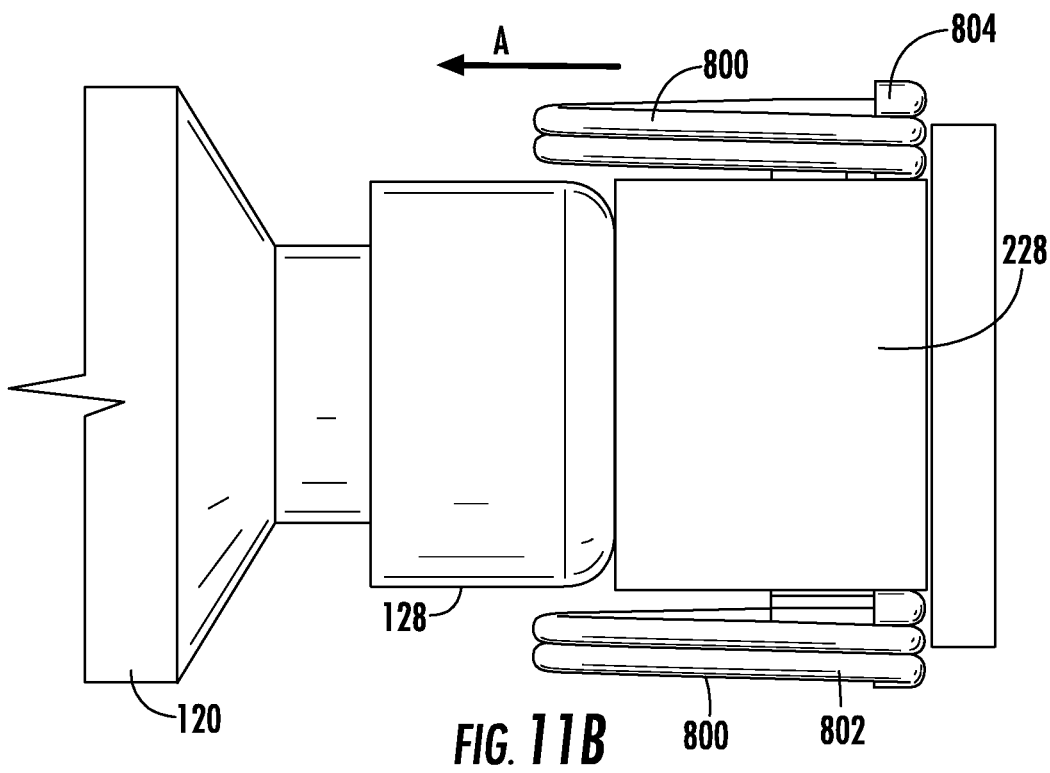
FIG. 11B illustrates a detailed, side view of the septum piercing mechanism shown in FIG. 11A.

FIGS. 11A and 11B illustrate a seventh example embodiment of a septum piercing mechanism in accordance with the disclosure. In this embodiment, the septum piercing mechanism may include a biasing or spring member 800. The biasing or spring member 800 may be, for example, but not limited to, first and second torsion springs 802, 804 disposed on opposite sides of the needle support 228. In use, the spring member 800 of this embodiment functions similarly to previous embodiments to bias the needle support 228 in the direction of arrow "A" toward the drug container 120 to facilitate piercing of the septum 130 when the drug delivery device 100 is activated.

Figure 12A:
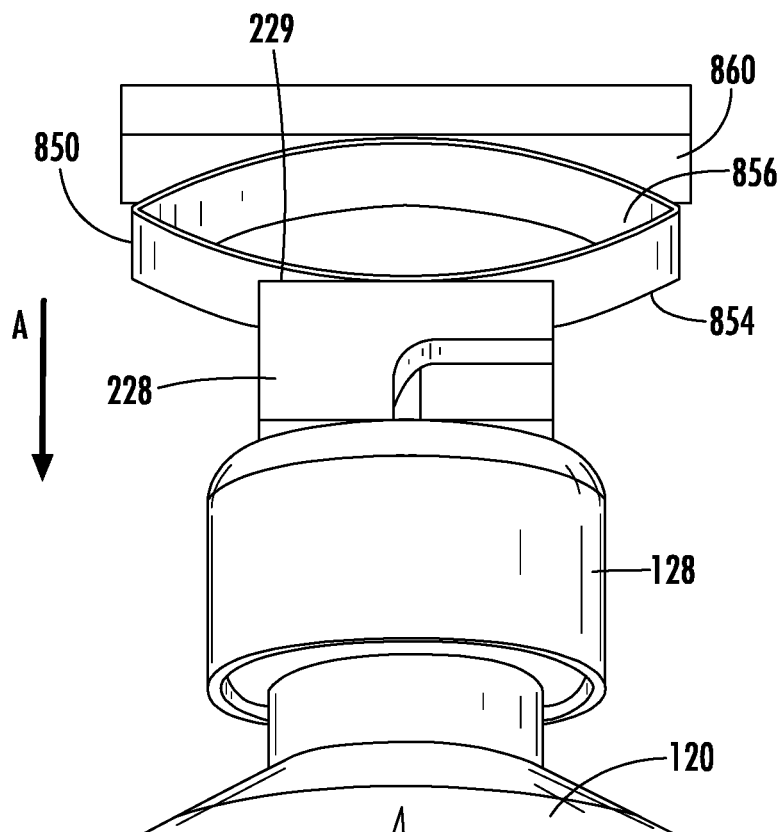
FIG. 12A illustrates a detailed, top view of an eighth example embodiment of a septum piercing mechanism in accordance with the disclosure, the septum piercing mechanism shown in the second or activated configuration.
Figure 12B:
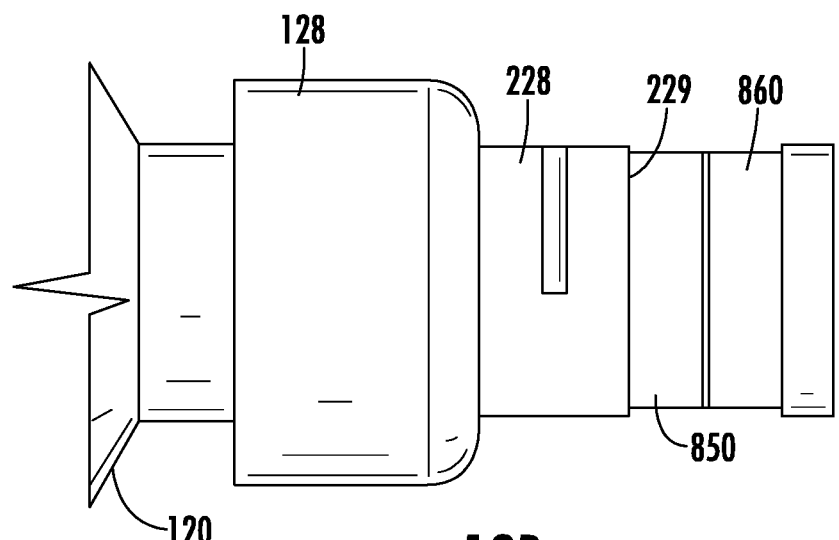
FIG. 12B illustrates a detailed, side view of the septum piercing mechanism shown in FIG. 12A.

FIGS. 12A and 12B illustrate an eighth exemplary embodiment of a septum piercing mechanism in accordance with the disclosure. In this embodiment, the septum piercing mechanism may include a biasing or spring member 850. The biasing or spring member 850 may be, for example, but not limited to a leaf spring. In use, the spring (e.g., leaf spring) 850 may be stacked between a top surface 229 of the needle support 228 and a bearing surface 860 disposed on the interior of the drug delivery device 100. In use, the spring (e.g., leaf spring) 850 may be formed via a plurality of sheet metal stampings 854, 856 that, in use, act like a leaf spring, and function similarly to previous embodiments to bias the needle support 228 in the direction of arrow "A" toward the drug container 120 to facilitate piercing of the septum 130 when the drug delivery device 100 is activated.

FIGS. 13A-13C illustrate a ninth exemplary embodiment of a septum piercing mechanism in accordance with the disclosure. In this embodiment, the septum piercing mechanism may include a biasing or spring member 900. The biasing or spring member 900 may be, for example, but not limited to, a conical spring. In use, the spring (e.g., conical spring) 900 may be positioned and compressed between a top surface 229 of the needle support 228 and a bearing surface 902 disposed on the interior of the drug delivery device 100. The spring (e.g., conical spring) 900 may act similarly to previous embodiments to bias the needle support 228 in the direction of arrow "A" toward the drug container 120 to facilitate piercing of the septum 130 when the drug delivery device 100 is activated.

Figure 14A:
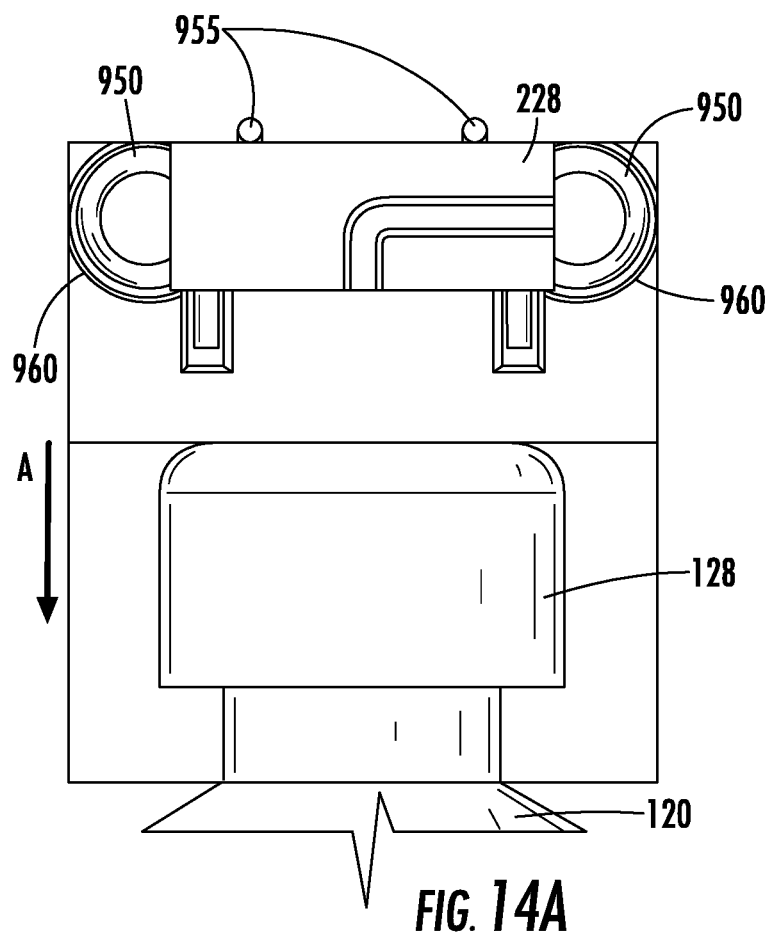
FIG. 14A illustrates a detailed, top view of a tenth example embodiment of a septum piercing mechanism in accordance with the disclosure.
Figure 14B:
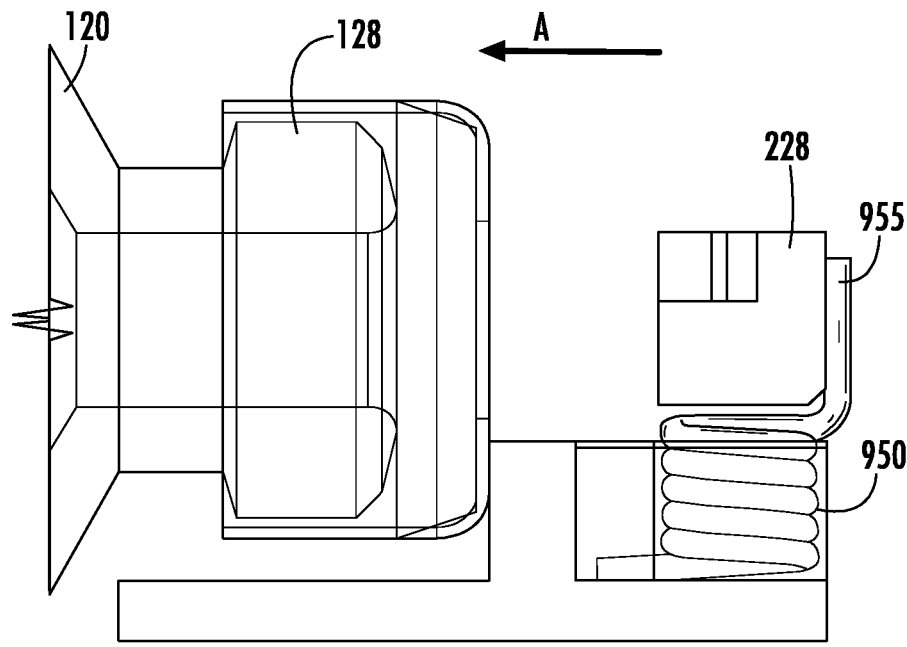
FIG. 14B illustrates a detailed, side view of the septum piercing mechanism shown in FIG. 14A.

FIGS. 14A and 14B illustrate a tenth example embodiment of a septum piercing mechanism in accordance with the disclosure. In this embodiment, the septum piercing mechanism may include a biasing or spring member 950. The biasing or spring member 950 may be, for example, but not limited to, first and second torsion springs. In use, the needle support 228 may be biased toward the drug container 120 in the direction of arrow "A" via first and second springs (e.g., first and second torsion springs) 950, which may reside in first and second respective grooves 960 formed in an internal structure of the drug delivery device 100. Each of the first and second springs (e.g., first and second torsion springs) 950 may include a leg 955 which overlies the needle support 228 to bias the needle support 228 toward the drug container 120. In a first or unactivated configuration or state, the end 142 of the needle conduit 140 is separated from the liquid drug 121 in the drug container 120 via the septum 130 and in the second or activated configuration or state, the end 118 of the needle conduit 140 is moved in the direction of arrow "A" due to the force supplied by the springs (e.g., first and second torsion springs) 950 to the needle support 228 to pierce the septum 130 to expose the needle conduit 140 to the liquid drug 121.

Figure 15:
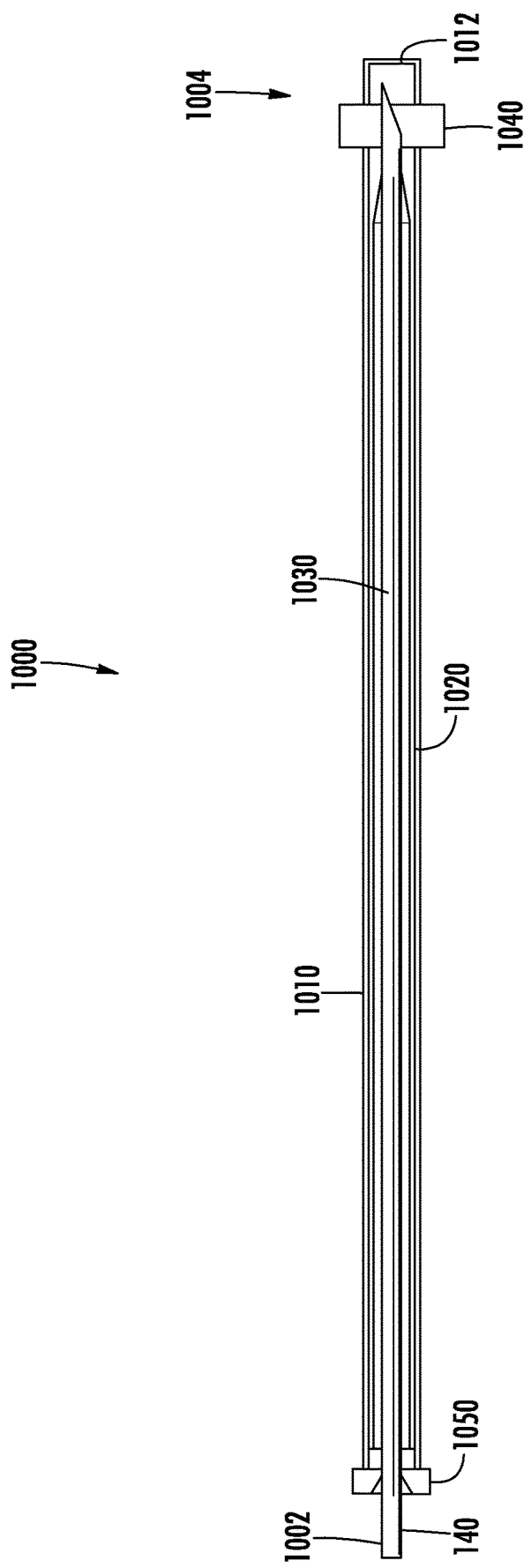
FIG. 15 illustrates a cross-sectional side view of an example embodiment of a patient injection needle tip septum piercing mechanism in accordance with an alternate aspect of the present disclosure.

In accordance with another aspect of the present disclosure, a patient injection needle tip septum piercing assembly for maintaining the sterility of the needle tip for insertion into a patient's body is disclosed. Referring to FIG. 15, the patient injection needle tip septum piercing assembly 1000 acts to seal the second or patient injection end 1004 of the fluid path (e.g., needle conduit) 1002. In use, the patient injection needle tip septum piercing assembly 1000 assists with maintaining the sterility of the surfaces and the fluid path intended to enter a patient's body.

As such, drug delivery devices, when used in combination with the patient injection needle tip septum piercing assembly 1000 of the present embodiment and one of the septum piercing mechanisms previously described enables both ends of the fluid path to be sealed to maintain sterility of the fluid path after sterilization and prior to final non-aseptic assembly. However, the patient injection needle tip septum piercing assembly 1000 of the present embodiment and the septum piercing mechanisms for piercing the septum of a drug container as previously described are stand-alone concepts, independent of one another. Thus, it is envisioned that the patient injection needle tip septum piercing assembly 1000 of the present embodiment may be used in combination with one of the septum piercing mechanisms described above or as stand-alone assembly, and vice-versa.

Referring to FIG. 15, the patient injection needle tip septum piercing assembly 1000 may include an outer body or tube 1010, an inner body or cannula 1020, and a needle 1030. The inner body or cannula 1020 may be disposed within the outer body or tube 1010. In addition, the inner body or cannula 1020 may receive at least a portion of the fluid path, for example, the second or patient injection end of the fluid path, for example, the injection end of the needle conduit 140. The outer body or tube 1010 may be adapted and configured as a collapsible tube with a pierceable seal 1012 at an end thereof. In one embodiment, the outer body or tube 1010 may be slide over the intended sterile zone and joined to the inner cannula 1020. In an alternate embodiment, it is envisioned that the inner cannula 1020 may be omitted, in such case the outer body or tube 1010 may be joined directly to the needle 1030.

The patient injection needle tip septum piercing assembly 1000 may also include a first support member 1040 operatively associated with or coupled to the outer body or tube 1010. As illustrated, in one embodiment, the first support member 1040 may be coupled to the outer body or tube 1010 adjacent to the second or patient injection end. The patient injection needle tip septum piercing assembly 1000 may also include a second support member 1050 operatively associated with or coupled to the inner cannula 1020 and the fluid path, for example, the needle conduit 140. As illustrated, in one embodiment, the second support member 1050 may be coupled to the inner cannula 1020 and the fluid path downstream of the first support member 1040 and the second or patient injection end. In this manner, in use, the needle 1030 and the inner cannula 1020 may be driven through the pierceable seal 1012 at the distal end of the fluid path and into the patient's body at the time of use, for example, at the time the drug delivery device is activated.

Incorporation of the patient injection needle tip septum piercing assembly 1000 enables the injection needle to be sealed, while preventing accidental breach of the seal. In use, the outer seal (e.g., the outer body or tube 1010) may cover at least the length of the inner cannula 1020 that enters the patient's body. Upon activation, the inner cannula 1020 and the needle 1030 are driven forward and through the seal 1012 formed on the distal end of the outer body or tube 1010. The injection needle 1030 may be driven forward by any suitable means.

In one embodiment, the seal 1012 may be rigidly supported at the distal end of the outer body or tube 1010 where piercing occurs so that a body portion of the seal 1012 collapses (e.g., buckles) to allow the inner cannula 1020 and the needle 1030 to pierce through the seal and enter the patient's body.

In one embodiment, the seal 1012 can be made of the same material as the inner cannula such that the two pieces can be joined. Once sealed, the fluid path can be sterilized prior to fill and maintain sterility until use.

Incorporation of the patient injection needle tip septum piercing assembly 1000 addresses maintaining a sterile fluid path in a drug delivery device using non-aseptic assembly methods and allows for standard filling processes of the drug cartridge to be used and avoiding aseptic assembly or secondary sterilizations with the drug present, thus avoiding the risks and costs associated with such processes.

In addition, incorporation of the patient injection needle tip septum piercing assembly 1000 provides numerous other advantages. For example, it assists to maintain a sterile seal at the second or patient injection end of the fluid path over the entire length of the needle being inserted, it allows the needle to pierce the seal without requiring removal of the seal by the user, it facilitates assembly to the fluid path and the drug container prior to filling, it reduces the number of required components thus reducing cost, weight, size, etc., etc.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. Accordingly, it is intended that the present disclosure not be limited to the described embodiments, but that it has the full scope defined by the language of the following claims, and equivalents thereof.

The phrases "at least one", "one or more", and "and/or", as used herein, are open-ended expressions that are both conjunctive and disjunctive in operation. The terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., engaged, attached, coupled, connected, and joined) are to be construed broadly and may include intermediate members between a collection of elements and relative to movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another. The drawings are for purposes of illustration only and the dimensions, positions, order and relative to sizes reflected in the drawings attached hereto may vary.

The invention claimed is:

1. A drug delivery device, comprising:
    a drug container including a liquid drug and a septum at one end of the drug container for sealing the liquid drug within the drug container;
    a needle insertion mechanism for insertion into a patient for administering the liquid drug;
    a needle conduit having a first end operatively associated with the drug container, and a second end coupled to the needle insertion mechanism; and
    a septum piercing mechanism for piercing the septum of the drug container, the septum piercing mechanism including:
        a needle support operatively coupled with the first end of the needle conduit;
        a biasing member operatively coupled to the needle support to bias the needle support towards the drug container; and
        a trigger block and a trigger lever operatively associated with the needle support to control movement of the needle support relative to the drug container, wherein the trigger block includes a first end surface and a second end surface, wherein the trigger lever is in direct physical contact with the first end surface to support the trigger block and the second end surface is in direct physical contact with the needle support when the septum piercing mechanism is in an unactivated configuration, wherein the needle support includes a set of legs straddling the second end surface of the trigger block, wherein the set of legs extend within a corresponding set of channels of an internal wall of the septum piercing mechanism, wherein in the unactivated configuration, the first end of the needle conduit is separated from the liquid drug stored in the drug container via the septum, and wherein in an activated configuration, the first end of the needle conduit pierces through the septum so that the needle conduit is in fluid communication with the liquid drug stored in the drug container.

2. The drug delivery device of claim 1, wherein:
    in the unactivated configuration, the needle support is prevented from moving towards the drug container; and
    in the activated configuration, the needle support is permitted to move towards the drug container such that the first end of the needle conduit pierces the septum, exposing the first end of the needle conduit to an interior portion of the drug container.

3. The drug delivery device of claim 1, wherein the drug container is fixedly positioned within the drug delivery device such that the drug container does not move as the septum piercing mechanism is transitioned from the unactivated configuration to the activated configuration.

4. The drug delivery device of claim 1, wherein the trigger block is operatively associated with the needle support to prevent the needle support from moving towards the drug container in the unactivated configuration,
    wherein the trigger lever is operatively associated with the trigger block, the trigger lever being movable between first and second positions, and
    wherein movement of the trigger lever from the first position to the second position enables the trigger block to move out of contact with the needle support so that the needle support can move towards the drug container.

5. The drug delivery device of claim 4, wherein the second end surface of the needle support includes an angled surface in slidable engagement with a corresponding angled surface of the trigger block so that when the trigger lever is moved towards the second position, a force from the angled surface of the needle support on the corresponding angled surface of the trigger block causes the trigger block to move away from the needle conduit.

6. The drug delivery device of claim 5, wherein the biasing member comprises first and second torsion springs mounted on either side of the needle support.

7. The drug delivery device of claim 6, wherein the first and second torsion springs each include a first leg for bearing against an internal surface of the drug delivery device and a second leg for bearing against and biasing the needle support toward the drug container.

8. The drug delivery device of claim 1, wherein the biasing member is selected from one of a torsion spring, a leaf spring, and a conical spring.

9. The drug delivery device of claim 8, wherein the biasing member is positioned between the needle support and one or more interior portions of the drug delivery device.

* * * * *